(12) United States Patent
Hallinan et al.

(10) Patent No.: US 6,552,221 B1
(45) Date of Patent: Apr. 22, 2003

(54) PROCESS CONTROL FOR ACETIC ACID MANUFACTURE

(75) Inventors: Noel Hallinan; James A. Hinnenkamp; Javan Shelly, all of Cincinnati, OH (US)

(73) Assignee: Millenium Petrochemicals, Inc., Cincinnati, OH (US)

( * ) Notice: Subject to any disclaimer, the term of this patent is extended or adjusted under 35 U.S.C. 154(b) by 0 days.

(21) Appl. No.: 09/672,893

(22) Filed: Sep. 29, 2000

Related U.S. Application Data

(63) Continuation-in-part of application No. 09/611,067, filed on Jul. 6, 2000, which is a continuation-in-part of application No. 09/216,330, filed on Dec. 18, 1998, now Pat. No. 6,103,934.

(51) Int. Cl.[7] .......................... C07C 51/12; C07C 51/10
(52) U.S. Cl. ....................................... 562/519; 562/517
(58) Field of Search .................................. 562/519, 517

(56) References Cited

U.S. PATENT DOCUMENTS

| | | |
|---|---|---|
| 3,772,156 A | 11/1973 | Johnson et al. |
| 4,000,170 A | 12/1976 | Forster et al. |
| 4,029,553 A | 6/1977 | Price |
| 4,039,395 A | 8/1977 | Eby |
| 4,102,922 A | 7/1978 | Price |
| 4,627,008 A | 12/1986 | Rosenthal |
| 5,121,337 A | 6/1992 | Brown |
| 5,227,520 A | 7/1993 | Cooper |
| 5,317,379 A | 5/1994 | Ryan et al. |
| 5,352,415 A | 10/1994 | Ochiai |
| 5,371,286 A | 12/1994 | Blay et al. |
| 5,374,774 A | 12/1994 | Ochiai |
| 5,416,237 A | 5/1995 | Aubigne et al. |
| 5,468,961 A | 11/1995 | Gradon et al. |
| 5,596,992 A | 1/1997 | Haaland et al. |
| 5,599,976 A | 2/1997 | Scates et al. |
| 5,604,132 A | 2/1997 | Capuano et al. |
| 5,625,095 A | 4/1997 | Miura et al. |
| 5,691,701 A | 11/1997 | Wohlstein et al. |
| 5,723,660 A | 3/1998 | Morimoto et al. |
| 5,750,007 A | 5/1998 | Clode et al. |
| 5,773,642 A | 6/1998 | Denis et al. |
| 5,783,731 A | 7/1998 | Fisher et al. |
| 5,817,869 A | 10/1998 | Hinnenkamp et al. |
| 5,831,120 A | 11/1998 | Watson et al. |
| 5,847,204 A | 12/1998 | Nobel |
| 5,874,610 A | 2/1999 | Clode et al. |
| 5,877,348 A | 3/1999 | Ditzel et al. |
| 5,883,295 A | 3/1999 | Sunley et al. |
| 5,916,422 A | 6/1999 | Kimura et al. |
| 5,932,764 A | 8/1999 | Morris et al. |

FOREIGN PATENT DOCUMENTS

| | | |
|---|---|---|
| EP | 0 487 284 | 4/1995 |
| EP | 0 983 792 | 3/2000 |
| EP | 0 985 653 | 3/2000 |
| JP | 2000-167303 A | 6/2000 |
| WO | WO 98/17619 | 4/1998 |
| WO | WO 98/22420 | 5/1998 |

OTHER PUBLICATIONS

J.A. Dean,*Analytical Chemistry Handbook*, McGraw Hill, Inc. 1995.
ASTM Designation: E 1655—97, *Standard Practices for Infrared, Multivariate, Quantitative Analysis*, Annual Book of ASTM Standards, vol. 14 pp 844–869.
Lavine et al., *Chemometrics Brightens the Future of Spectroscopy*, American Chemical Soc., Today's Chemist at Work, Oct. 1997 pp 29–37.
Workman Jr. et al., *A New Standard Practice for Multivariate, Quantitative Infrared Analysis—Part I*, Spectroscopy 11(2) Feb 1996 pp 48–51.
Doyle, *Principles and Applications of Fourier Transform Infrared (FTIR) Process Analysis*, Process Control and Quality, 2 (1992) 11–41, Elsevier Science Publishers BV, Amsterdam.
Workman Jr. et al., *A New Standard Practice for Multivariate, Quantitative Infrared Analysis—Part II*, Spectroscopy 11(9) Nov./Dec. 1996 pp 24–29.
Doyle, *Near–IR and Mid–IR Process Analysis—A Critical Comparison*, ISA–95 5617–1099/95 115–131.
Coates, *Meeting the Needs of Process Spectroscopy Applications*, Spectroscopy, 10(6) Jul./Aug. 1995 pp 27–30.
Coates, *Development of a Near–Infrared Analyzer for Refinery Analysis*, Spectroscopy 9(9) Nov./Dec. 1994 pp 36–40.
Workman Jr. et al., *Selecting the Calibration Samples*, Spectroscopy 7(6) Jul./Aug. 1992 pp 16–19.
Mark et al., *Chemometrics in Spectroscopy: Experimental Designs, Part I*, Spectroscopy 9(8) Oct. 1994 pp 26–27.
Coates, *Process Analytical Instrumentation*, Spectroscopy 10(2) Feb. 1995 pp 28–31.
Brereton, *Chemometrics—Linear Smoothing Functions and Filters*, htt://chemweb.com/alchem/1999/molmodel/cm_991126.html, 3 pp.
Streitweiser & Heathcock, *Introduction to Organic Chemistry, 2nd Ed., Appendix VI, Infrared Bands*, McMillan, pp 1200–1202.
Doyle, Axiom Monitor, No. 1, 2 pp.

Primary Examiner—Paul J. Killos
(74) Attorney, Agent, or Firm—Wood, Herron & Evans, LLP

(57) ABSTRACT

A method of real time process control in a reaction system for the production of acetic acid from the carbonylation of methanol. Reaction system samples are collected from columns and/or transfer lines downstream of a reactor vessel, and the concentration of one or more components in the sample is measured by an infrared analyzer. The concentration measurements are then used to make adjustments in the concentration of components in the reaction system, directly or indirectly, such as by adjusting the temperature profile in a particular column, the flow rate of solution in to or out of a column, the vent gas rate out of the reactor or a column, or the addition or extraction of a component to or from the solution. For optimum process control, the measurements are transmitted to a control unit for real time analysis, and the adjustments are made substantially instantly after the infrared analysis.

73 Claims, 10 Drawing Sheets

PROCESS CONTROL FOR ACETIC ACID MANUFACTURE

CROSS-REFERENCE TO RELATED APPLICATIONS

This application is a continuation-in-part of U.S. patent application Ser. No. 09/611,067 filed Jul. 6, 2000 allowed and entitled which is a continuation-in-part of U.S. patent application Ser. No. 09/216,330, now U.S. Pat. No. 6,103,934, filed Dec. 18, 1998 and entitled MANUFACTURING AND PROCESS CONTROL METHODS.

FIELD OF THE INVENTION

This invention relates to a method of improving process control in the manufacture and purification of acetic acid, and a method of manufacturing acetic acid utilizing improved process control.

BACKGROUND OF THE INVENTION

The prevailing method of acetic acid production involves continuously reacting methanol and carbon monoxide in a stirred reactor. The reaction mixture contains a soluble catalyst from Group 9, specifically iridium or rhodium, and methyl iodide/hydrogen iodide promoters which accelerate the rate of reaction. The two primary reactions which occur in the acetic acid process involve the carbonylation of methanol with carbon monoxide to form acetic acid and a water gas shift reaction which forms carbon dioxide and hydrogen from carbon monoxide and water. Hydrogen production from the water gas shift reaction further leads to the formation of a propionic acid impurity in the reactor solution.

A complex network of dependent equilibria involving liquid acetic acid reaction components exists in the reactor. Even slight changes in these equilibria can induce considerable and adverse effects on catalyst stability and activity in the reactor. These changes can ultimately lead to compositional changes in liquid streams entering the purification section of an acetic acid plant practicing methanol carbonylation technology.

The use of on-line infrared analysis in controlling reactor liquid composition has been described in U.S. Pat. No. 6,103,934 entitled MANUFACTURING AND PROCESS CONTROL METHODS, and U.S. patent application Ser. No. 09/611,067 filed Jul. 6, 2000 and entitled MANUFACTURING AND PROCESS CONTROL METHODS, each incorporated herein by reference in their entirety. Real time analysis of reactor solution allows instant adjustments to be made via process control loops to effect optimal reactor performance. In the process of acetic acid production and purification, it is of course necessary to remove other components from the acetic acid products and, where necessary, return these other components via recycle loops to the reactor or other parts of the process. The composition of these purification/recycle streams is partially a function of reactor composition/performance and partially a function of recycle/purification column performance.

There is thus a need to implement process control via on-line infrared analysis to the purification and recycling section of an acetic acid reaction system, such as in a manufacturing plant.

SUMMARY OF THE INVENTION

The present invention provides a method of real time process control of component concentrations in a reaction system for the production of acetic acid from the carbonylation of methanol. To this end, and in accordance with the present invention, samples of reaction system solution are collected from columns and/or transfer lines downstream of a reactor vessel, and the concentration of one or more components in the sample is measured by an infrared analyzer. The concentration measurements are used to make adjustments in the process. The concentration of one or more components is adjusted, either directly or indirectly, in one or more locations in the reaction system in response to the downstream measurements. For example, the flow rate of a solution stream in a transfer line can be increased or decreased going into or out of a column to alter the concentration of one or more of the components in that column or another vessel in the reaction system. Alternatively, the temperature of the solution in a column or stream or the temperature profile or gradient in a column could be increased or decreased to affect the concentration of one or more components in the reaction system solution. Also, the concentration of a reaction system component can be adjusted directly by direct addition or extraction of that component into or out of the solution. For example, water concentration in the reaction system can be adjusted directly by increasing or decreasing the water feed into the reactor vessel, and indirectly by increasing or decreasing recycle streams containing water to the reaction section. The vent gas rate out of the reactor vessel or a column can also be increased or decreased. Thus, reaction system component concentrations can be adjusted directly or indirectly by varying any number of process variables in the reaction system. Further, adjustment in one location of the reaction system may cause concentration changes at either that location or upstream or downstream of that location. For optimum process control, the measurements are transmitted to a control unit for real time analysis, and the adjustments are made substantially instantly after the infrared analysis. There is thus provided a method for continuously updating the conditions of the reaction system to enhance process control in real time of the overall process to thereby optimize the production and purification of acetic acid product.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

A. The Acetic Acid Reaction System

Figure 1:
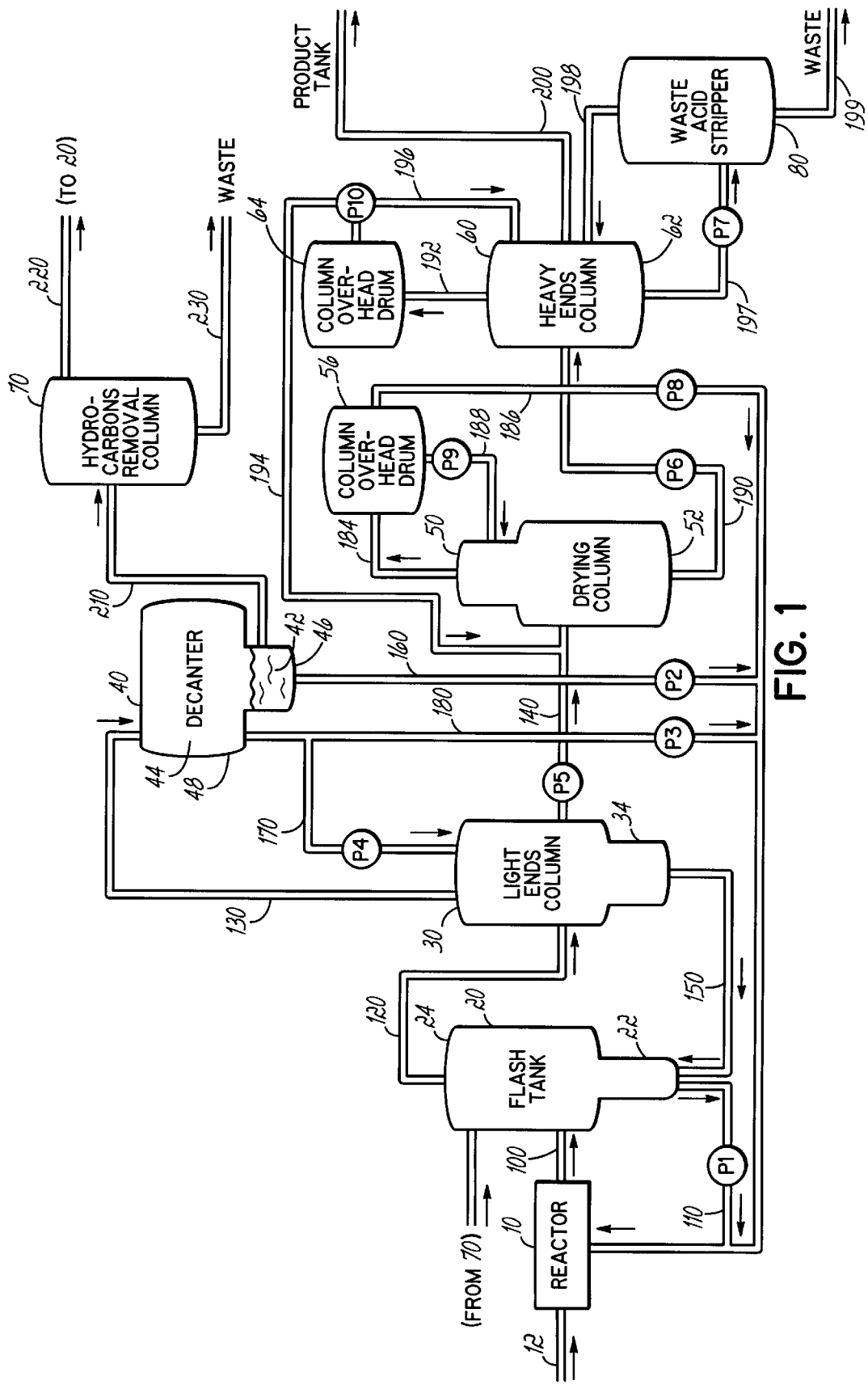
FIG. 1 is a schematic representation of an acetic acid manufacturing plant.

An acetic acid manufacturing plant practicing methanol carbonylation technology, as depicted schematically in FIG. 1, can be conveniently divided into three functional areas: reaction, light ends recovery, and purification. Acetic acid reaction systems may vary in the type and number of distillation columns, for example as described in U.S. Pat. Nos. 3,772,156, 4,039,395, 5,831,120, 5,227,520, 5,416,237 and 5,916,422 and in PCT publication WO9822420, and such variations, which are within the skill of one of ordinary skill in the art, are included within the scope of this invention. In general, the reaction section consists of a reactor 10 and flash tank 20. The light ends recovery section consists of a light ends column 30 and a phase separation vessel 40 (decanter). The purification section consists also of the light ends column 30, as well as a drying column 50 and optionally a heavy ends column 60. The various columns and vessels are connected by transfer lines, such as pipes, through which the reaction system solutions flow, typically with the aid of pumps. For ease of depiction and discussion, the transfer lines and streams therein are referred to herein as one in the same, using the term "stream".

The feed to the reactor 10 is via stream 12 comprised of methanol, dimethyl ether, methyl acetate or mixtures thereof. Water may also be present in stream 12. Carbon monoxide or mixtures with inert gases are also fed to the process via stream 12. During normal reactor 10 operation, reactor contents are continuously withdrawn as a liquid. This is achieved by flashing reactor solution across a valve (not shown) to produce a vapor-liquid stream 100 which is sent to the flash tank 20 where vapor is separated from the liquid. The liquid, containing catalyst, accumulates in the bottom 22 of the flash tank 20 and is pumped back into the reactor 10 via stream 110 by a catalyst recycle pump P1. The vapor stream 120 leaving the top 24 of the flash tank 20 contains the acetic acid product, water, methyl iodide (MeI), hydrogen iodide (HI), and low levels of impurities, i.e. propionic acid and acetaldehyde. This vapor is fed to the light ends column 30. Thus, the primary purpose of the flash tank 20 is to separate the catalyst from the crude product and allow the catalyst to be returned to the reactor 10.

The light ends column 30 is critical to the overall process as it serves the dual purpose of crude acetic acid purification and of recycling iodide back to the reaction section. The light ends column 30 is fed from the overhead vapor stream 120 from the flash tank 20. It allows separation of the higher boiling acetic acid from the lower boiling components such as MeI and methyl acetate (MeOAc). Three streams 130, 140,150 are removed from the light ends column 30. The overhead stream 130 consists primarily of MeI but also contains some water, MeOAc and acetic acid and is sent to a phase separator or decanter 40 described below. A sidedraw stream 140 from the light ends column 30 consists of wet acetic acid, which is sent to the drying column 50 by pump P5. The light ends bottoms stream 150 consists of water, HI and acetic acid, which are recycled to the reaction section, which encompasses the reactor 10 and flash tank 20.

The second part of the light ends recovery section is the phase separator 40, more commonly called the decanter. In this decanter 40, a heavy phase 42 consisting primarily of MeI and an immiscible light phase 44 consisting primarily of aqueous acetic acid are separated. The primary purpose of this separation of light phase 44 and heavy phase 42 is to recycle MeI to the reactor 10. The MeI to be recycled collects in a small boot 46 of the decanter 40, the volume of which is much less than that of the remaining top portion 48 of the decanter 40 which contains the light phase 44. The MeI in boot 46 is recycled to reactor 10 by pump P2 via bottoms stream 160. A secondary purpose of the light phase separation is to return by pump P4 via stream 170 some of the light phase 44 as reflux to the light ends column 30, the remainder of the light phase 44 being recycled via stream 180 to the reactor 10 by pump P3. The amount of light phase directed to stream 170 versus stream 180 can be adjusted by one or both of pumps P3 and P4.

Many acetic acid processes contain additional processing of the heavy phase 42 and the light phase 44. In processes such as those described in U.S. Pat. Nos. 4,102,922, 5,371, 286 and 5,599,976, the heavy phase 42 is further treated to remove alkanes. One such process is shown in FIG. 1 where the hydrocarbons removal column 70 is fed by a portion of the heavy phase 42 via stream 210. The overhead of the column 70 is returned via stream 220 to the flash tank 20. The alkanes-rich bottoms are sent to waste via stream 230. A number of acetic acid processes have additional treatments of the heavy phase 42 and light phase 44 to remove impurities such as acetaldehyde and its condensation products. Examples of such acetaldehyde removal systems are described in U.S. Pat. Nos. 5,599,976, 5,723,660, 5,625,095 and 5,783,731, EP Patent No. 487,284 and PCT Publication WO9817619. All of the acetic acid process streams can be analyzed using the current invention to provide improved control of the individual processing steps as well as overall process control.

Purification encompasses the light ends column 30, as discussed above, as well as a drying column 50 and heavy ends column 60. Many acetic acid processes contain an additional column 80 to strip acetic acid from higher boiling impurities. The drying column 50 is a large distillation column which takes as its feed a wet acetic acid stream 140 from the light ends column 30 through pump P5. As its name implies, the primary purpose of the drying column 50 is to remove water from the product acetic acid. Water is removed overhead via stream 184 to a column overhead drum 56 and returned to the reaction section via stream 186 by pump P8. A portion of the condensed solution in drum 56 is returned as column reflux via stream 188 by pump P9. In some acetic acid processes such as that described in U.S. Pat. Nos. 5,599,976 and 5,723,660, a portion of the overhead stream 184 condensed in drum 56 is added via transfer line (not shown) to either the light ends column 30 or drying column feed stream 140. The current invention would offer improved process control of the processes described in the above patents. Dry acetic acid is removed from the bottoms 52 of the drying column 50 and is either pumped directly to product tanks (not shown) or to a heavy ends column 60 by pump P6 via stream 190 for further removal of impurities such as propionic acid. Additional acetic acid can be recovered from stream 197 which is fed to a waste acid stripper column 80 by pump P7. The recovered acetic acid is returned via stream 198 to heavy ends column 60. Waste propionic and higher acids are sent for disposal via stream 199. The overhead of heavy ends column 60 is sent via stream 192 to drum 64, condensed, and returned by pump P10 as reflux to the heavy ends column 60 via stream 196 or sent via stream 194 to be mixed with stream 140.

The purpose of the optional heavy ends column 60 is to remove higher boiling propionic acid impurity from acetic acid. The bottoms portion 62 of the heavy ends column 60 consists primarily of propionic acid while a sidedraw stream 200 consists of pure acetic acid which is sent to storage in a product tank.

B. Process Control

The generally accepted method of overall plant control is the concept of inventory control, also known as level control. This is primarily achieved in two areas, the reaction section and the light ends recovery section. In the reaction section, the flashing rate of reactor solution must be sufficient to match the reactor feed rate and thus maintain desired reactor solution level, as well as reaction temperature. A reactor cooler (not shown) is frequently used to help control reaction temperature as the flashing ratio is varied. In the light ends section, the inventory concept has two primary functions. The first function is to return MeI back to the reactor 10 with a minimum of inventory shift. Level controlling the heavy phase 42 in the boot 46 achieves this objective. The second function is to remove the correct amount of acetic acid from the light ends column sidedraw stream 140 and feed it forward to the drying column 50. Level controlling a sidedraw tray (not shown) of the light ends column 30 and flow controlling the decanter light phase recycle stream 180 to the reactor 10 accomplishes this objective. These two controls work together in that if more crude acetic acid needs to be fed forward via stream 140, the flow of the light phase recycle stream 180 to the reactor 10 is decreased. This forces more light phase reflux via stream 170 to the light ends column 30, which in turn forces more acetic acid down the column 30 to the level controlled sidedraw tray. Conversely, if less crude acid is to be removed from the system, the flow via stream 180 of the decanter 40 light phase recycle to the reactor 10 is increased. The result is lower column reflux via stream 170, more acetic acid in the overhead of column 30 and less acid on the sidedraw tray to be fed forward via stream 140. Another key control concept is to contain HI in the bottoms 34 of the light ends column 30. A minimum required water concentration in the bottoms 34 ensures that the HI remains below the sidedraw tray and is returned to the reaction section rather than moving forward to the drying column 50.

While the concept of inventory control works reasonably well in ensuring quality control, compositional changes can occur which may lead to undesirable conditions in the process. As some of these compositional changes may not be detected (or at least not detected in a timely fashion) by inventory control, it would be appreciated by one skilled in the art of acetic acid manufacture that continuous updates of component concentrations of various streams and columns would greatly benefit optimal operation of light ends recovery and purification sections. This is particularly the case in the practice of low water technology where water concentration in the various columns is critical to product purity, as will be described below.

Typically, downstream analysis is conducted by off-line sampling followed by laboratory analysis of some of these streams. These samples are obtained a few times daily and generally there is a lag of several hours between sampling and the stream composition data becoming available to plant operators. Also, while is off-line data helps in determining average column performance, it does not give any information on any possible cyclic behavior in any of these vessels. The cycling of the purification section can lead to breakthrough of impurities such as iodides into the product stream 200, which ultimately reaches the product storage tank. Such cyclic behavior might be invisible to infrequent daily sampling but will be readily apparent from continuous on-line data in accordance with the present invention.

The ability to analyze the various process streams and columns in a typical acetic acid plant such as that depicted in FIG. 1 allows for various levels of process control. Each vessel in the purification section can be controlled separately or in conjunction with each other. Each vessel can be controlled using a mass balance principle, namely that the mass flow into and out of the vessel can be adjusted based on the composition of the streams in and out so that the component or components being monitored can be controlled singly or in combination. Depending on the desired level of control required, it may also be necessary to change the temperature or temperature distribution in the distillation columns. Typically, this can be achieved by adjusting the steam flow to the column reboiler alone or in combination with column pressure. It is also sometimes necessary to additionally control columns that are before or after the column being controlled in a cascade-type of control scheme. Not only is the monitoring of the various streams possible by the current invention, but analysis probes can be inserted at key points throughout individual purification columns to provide information on component gradients within the column. Profile information of this type can be used to control the rate of change of column conditions to minimize upsets. The process control of the present invention may provide a significant advantage in the low water processes, such as described for example in U.S. Pat. Nos. 5,001,259, 5,026,908, 5,144,068, 5,750,007, 5,817,869 and 6,031,129.

While not specifically shown in FIG. 1, acetic acid plants typically employ reactive distillation techniques in some of the columns by injection of potassium acetate or methanol to scavenge iodides, for example as described in U.S. Pat. No. 3,772,156. The current invention allows the feed rate of the component being injected into the column to be controlled based on the analyses of the column profile, feed or outlet.

1. Process Control in the Light Ends Decanter

Conditions where continuous updates of the component concentrations in the light ends decanter vessel 40 are useful to process control are outlined below.

In cases where the reactor 10 is to be operated at low water and/or high MeOAc concentration, conditions in which MeI cannot be separated as a distinct phase in the decanter 40 should be avoided. If the water concentration in the light phase 44 falls to a low level, the light phase 44 becomes predominantly acetic acid, and an increasing amount of MeI becomes soluble in the light phase 44. In extreme cases, there exists only one phase in the decanter 40, which subsequently dilutes the MeI concentration to a low level throughout the entire decanter 40. As a result, the pump which is designed to recycle a phase that is high in MeI concentration is not able to recycle sufficient MeI to the reactor 10 to maintain reaction. As a result, the reactor 10 is "quenched" and the operating parameters need to be adjusted to resume the desired reaction. In addition, a high concentration of MeOAc in the light phase 44 allows MeI to dissolve in the light phase 44 to the extent that only one phase exists in the decanter 40. For example, if the continuous analysis of stream 160 shows that MeI concentration has decreased, the flow at pump P2 in FIG. 1 can be increased so that a constant amount of MeI is returned to the reactor 10.

The portion of the light phase 44 that is returned to the light ends column 30 as reflux also serves to balance the water load between the reactor 10 and the downstream drying column 50. If too much water is returned to the light ends column 30 by increasing the reflux via stream 170 and decreasing the recycle via stream 180 to the reactor 10, then more water is eventually removed in the sidedraws product takeoff and subsequently sent to the drying column 50 via stream 140. The water load in the drying column 50 can be increased to the extent that the column is flooded and will not perform its water removal function. Conversely, if too much water is sent through the recycle stream 180 to the reactor 10, the drying column 50 may be critically unloaded and allow impurities such as hexyl iodide to break through into the product stream 200. Another example of the analytical capabilities of the current invention is to control the light ends column 30 by ensuring the acetic acid and water concentration in sidedraw stream 140 is maintained. One example of a control scheme is to adjust the light ends column reboiler temperature alone or in conjunction with the column reflux 170 based on the acetic acid and water analyses.

Because the concentrations of water and/or MeOAc may change in the reactor and in the downstream areas, to either increase production rate or to change the quality of the product it is important to monitor the composition of both the light phase 44 and heavy phase 42, particularly to avoid the case where the decanter 40 contains only one phase. On-line analysis of the two phases 42,44 can inform operators of changes in composition that, if left uncorrected, may lead to conditions of one phase in the decanter 40. In particular, the concentration of water in the light phase 44 and the concentrations of MeOAc in both the light phase 44 and heavy phase 42 are parameters that can be used as guidelines to avoid undesirable conditions in the drying column 50. In addition to avoiding the condition of one phase in the decanter 40, knowledge of the water concentration can also be used to maintain the proper balance of water between the reactor 10 and the drying column 50. One example of an integrated control scheme based on multiple continuous analysis of heavy phase 42 and light phase 44 is given below. With reference to FIG. 1, if MeI concentration decreases in heavy phase 42 then the flow by pumps P2 and P3 is adjusted to maintain a constant amount of MeI returned to the reactor 10. Because a change in the flow of light phase 44 could affect the water balance in the reactor 10, the water analysis of light phase 44 is used to adjust the make-up water feed (not shown) to the reactor 10 so a constant water concentration is maintained.

Another embodiment of the current invention is application of the process control to the acetic acid processes described in U.S. Pat. Nos. 5,599,976 and 5,723,660. If the analyses of heavy phase 42 and light phase 44 indicate the imminent presence of a single phase, a portion of stream 186 which contained a high water concentration can be directed (not shown) to stream 120 or the decanter 40 to improve phase separation. Additionally the water balance in the decanter 40 can be maintained by adjusting the flow for pumps P3 and P4.

Hydrocarbons can sometimes build up in the heavy phase 42 with MeI. Carbon monoxide (CO) used in methanol carbonylation is generally sourced from incomplete combustion of natural gas or oil residues. As a result, CO streams may contain trace quantities of hydrocarbons, generally alkanes. These generally low boiling hydrocarbons will thus tend to concentrate in the decanter heavy phase 42 where they have a high degree of solubility. The density of lower alkanes is of the order of 0.7 g/mL and thus, as well as diluting the MeI in the heavy phase 42, the lower alkanes will tend to decrease the heavy phase density. As heavy phase separation is a function of both solute immiscibility and density, increasing hydrocarbon concentration may adversely affect decanter performance. As shown in FIG. 1, an alkane (hydrocarbon) removal column 70 receives a flow of heavy phase 42 including hydrocarbons and MeI via stream 210 from the boot 46 of decanter 40, MeI is separated and fed back to the reactor section via stream 220, whereas the hydrocarbons are removed via stream 230. Alkanes removal columns are known to those skilled in the art of acetic acid manufacturing and can be operated in a batch or continuous mode. On-line analysis of hydrocarbons would allow a determination of the appropriate flow of decanter heavy phase 42 to an alkanes removal column 70.

Acetaldehyde ($CH_3CHO$) is an undesired byproduct in the reactor 10. It can undergo hydrogenation in the reactor 10 to form ethanol, which may be subsequently carbonylated to form propionic acid, which is difficult to separate from acetic acid in the purification section. Acetaldehyde may also condense to give $C_4$, $C_6$, $C_8$ etc. alcohols, which will form the corresponding iodides. The $C_6$ iodide, hexyl iodide in particular, is troublesome in the practice of low water acetic acid manufacture technology as it is difficult to separate from acetic acid in the drying column 50 and may lead to iodide contamination of the acetic acid product, for example, as discussed in EP Publication No. 985,653.

Acetaldehyde has a boiling point of only 21° C. and thus will tend to accumulate in the light ends column 30 overhead and concentrate in the decanter 40. On-line analysis of this component in both decanter phases 42,44 would thus help in combination with on-line reactor analysis of other components, in identifying optimal reactor conditions to minimize byproduct formation. A variety of process modifications are known in the art for removing acetaldehyde, and the analytical methods described herein allow improved process control of any of these known processes. The concentration of acetaldehyde in reactor solution is too low to allow on-line analysis, but any acetaldehyde concentration changes in the decanter 40, where it can be monitored, can be reasonably expected to correlate with changes in the reactor 10.

2. Process Control in the Light Ends Column Bottoms

Hydrogen iodide (HI) forms a high boiling azeotrope in acetic acid solutions having greater than about 5 wt.% water. If the water concentration falls below about 5 wt.%, azeotropic breakdown and HI volatilization will begin to occur. Such volatilization will lead to less HI in the bottoms stream 150 returning to the reaction section, and thus, may adversely impact reactor iodide inventory. The volatilized HI will now principally become part of the light ends sidedraw stream 140 of wet acetic acid which feeds the drying column 50. Process equipment generally used in HOAc manufacture is substantially inert to the components, but may be corroded or otherwise adversely affected if HI concentration levels in the system reach excessively high levels. Thus, the presence of a significant concentration of HI in this feed has consequences both in terms of corrosion of purification vessels and in terms of iodide contamination of final acetic acid product. Thus, it is critical both in terms of reactor performance and purification section performance that the water level in the bottoms 34 of the light ends column 30 be maintained at a minimum concentration of about 5 wt.% (about 3 molar).

HI and water can be accurately measured by either extended mid-infrared (4000–7000 $cm^{-1}$) or mid-infrared (400–4000$cm^{-1}$) spectroscopy. Thus, on-line analysis of the light ends bottoms 34 will serve to indicate when water concentration may be reaching critically low levels and thus help avoid column upsets.

3. Process Control in Drying Column Feed and Drying Column

The drying column feed is the side stream 140 from the light ends column 30. This is primarily water and acetic acid with small quantities of MeI and MeOAc and trace quantities of HI. The main purpose of this column 50 is to produce dry acetic acid. Water is removed overhead via stream 184. However, the drying column 50 is not designed to produce a very pure overhead stream. The water composition in the overhead stream 184 should optimize the additional cost of recycling the acetic acid and the cost of separating the acetic acid from water. Some of this overhead stream 184 is recycled to the reactor 10 via stream 186 through pump P8 to maintain the system water inventory or as mentioned above can be used to feed water to the light ends column 30 and decanter 40.

The drying column 50 is operated on the temperature gradient concept and has a number of liquid loaded trays (not shown). On-line analysis of water in the drying column feed 140 and in these trays would give an instantaneous and continually updated water profile of this column 50. The availability of such a profile would serve a number of purposes. If too much water is being sent to the drying column 50 from the light ends column sidedraw stream 140, the water load in the drying column 50 can be increased to the extent that the column is flooded and will not perform its water removal function. Conversely, if too much water is sent to the recycle via stream 150 to the reactor 10, the drying column 50 may become unloaded. A combination of on-line water analysis of light ends bottoms 34, light ends sidedraw into stream 140 and of drying column trays would allow any undesired decrease or increase in column loading to be quickly identified and addressed.

A second advantage of a water profile of the drying column 50 is associated with low water technology. Hexyl iodide, a minor byproduct, forms a constant boiling azeotrope with acetic acid and water and hence is difficult to remove by distillation. Furthermore, the volatility of this azeotrope decreases with decreasing water concentration with the potential for increased iodide contamination in the bottoms 52 of the drying column 50. This water profile concept applied to the drying column 50 is described for example in EP Publication No. 985,653, and the present invention provides a method of improved control of the water profile of the drying column 50 useful in association therewith. Hexyl iodide is present at the parts per billion (ppb) level, too low for detection or quantization by FTIR, but a knowledge of the column water content versus azeotropic breakdown water concentration will allow on-line analysis of water to be used as a means of controlling iodide contamination in the acetic acid product. Such dynamic control would negate the need for a dedicated iodide removal column and thus lead to significant cost savings.

4. Process Control in the Heavy Ends Column

The primary purpose of the heavy ends column 60 is to remove propionic acid impurity from the acetic acid. The bottom portion 62 of this column is a low volume stream of propionic acid, while the pure acetic acid is taken off in a sidedraw stream 200. Extended mid-infrared analysis allows propionic acid to be quantified down to about 200 ppm, either by a transmission cell or by a fiber optic coupled probe. Typically, the feed from stream 190 to the heavy ends column 60 could include about 200–1000 ppm of propionic acid. Thus, analysis of the feed stream 190 and of the acetic acid sidedraw stream 200 would allow the column performance to be monitored and allow a continual update of acetic acid product purity in terms of propionic acid content. This analysis would also permit the water concentration to be quantified down to about 100 ppm. Pure acetic acid product normally contains about 100–500 ppm water.

Another example of process control is the control of the amount of condensed stream 192 that is recycled from overhead drum 64 by pump P10 via stream 194 to stream 140 versus column reflux stream 196 based on the propionic concentration of stream 200. In addition to the flow of the two streams 194, 196, the column reboiler temperature can be adjusted.

Propionic and higher acids are present along with a substantial concentration of acetic acid in the heavy ends column bottoms 62. Additional acetic acid can be recovered from the bottoms 62 by feeding stream 197 to waste acid stripper column 80. Analysis of waste stream 199 can be used to optimize heavy ends column temperature and the flow by pump P7 to maximize acetic acid recovery and minimize waste for disposal.

C. Calibration Modeling

Infrared calibration models were obtained using chemometric techniques as described in U.S. Pat. No. 6,103,934 and U.S. patent application Ser. No. 09/611,067, expressly incorporated by reference herein in their entirety. Chemometrics is a branch of chemical analysis utilizing statistics wherein algorithmic relationships and mathematical logic are incorporated to obtain a calibration model involving multi-variate analysis. The term multi-variate analysis refers to the relation of the concentration of a component in a solution to many infrared wavelengths or frequencies. Software products are commercially available which permit ready application of chemometric techniques. Representative products include PIROUETTE™, from Infometrix, Seattle, Wash. The general steps involved in developing chemometric calibration models are well known to those skilled in the art. Also, the American Society for Testing and Materials (ASTM) has published a document titled "Standard Practices for Infrared Multivariate Analyses (No. E1655-94)", incorporated herein by reference in its entirety, in which recommended guidelines are provided.

To obtain a good chemometric calibration model it is important to properly choose the calibration standards. A large number of calibration standards may need to be prepared and analyzed where there is a broad weak signal for the component of interest which is overlapped with signals from other components. The number can be in the range of 30 to 300. To create an accurate calibration model, a number of calibration standards are prepared, each containing all of the components normally present in the reaction system solution. Some or all of these components are to be eventually analyzed by infrared spectroscopy. The components of individual standards are independently varied by concentration to randomize any bias or interferences that one component might have on another. The maximum and minimum concentration values expected in the reaction system solution serve as the boundary limits for the individual component concentrations. After the standards are prepared they are sequentially injected into the infrared analyzer and a spectroscopic signal is collected. Generally, the individual spectra for the calibration standards are first converted into digitized format and then set up in a spreadsheet with the corresponding concentrations of the component which is to be measured. Partial Least Squares (PLS) regression methods are then used to fit the data. Ultimately the accuracy of the calibration model is tested by comparing concentrations of the reaction system components obtained from an on-line analyzer during an actual process run with the concentrations obtained by actually sampling the various streams and columns and analyzing for component concentration using independent off-line analytical methods.

The spectral regions used in obtaining calibration models for each component in the extended mid-infrared, which is from 7000 $cm^{-1}$ to 4000 $cm^{-1}$, and in the mid-infrared, which is from 4000 $cm^{-1}$ to 400 $cm^{-1}$, are shown in Table 1.

TABLE 1

Extended Mid-Infrared (using Transmission cell) and Mid-Infrared (using Attenuated Total Reflectance cell) Spectral Regions Used for Quantitative Analysis of Light Ends Recovery and Purification Streams/Vessels

| Vessel/ Stream | Component | Extended Mid ($cm^{-1}$) | Mid ($cm^{-1}$) |
|---|---|---|---|
| Decanter (Heavy Phase) | MeI | 6261–5351 | 2520–2420 |
| | HOAc | 6980–5342 | 1944–1567 |
| | MeOAc | 6210–5505, 4730–4240 | 1944–1567, 1131–991 |
| | Hydrocarbons | 4412–4240 | 3550–2390 |
| | $H_2O$ | 5375–4700 | 4018–2370, 2046–1536 |
| | $CH_3CHO$ | 6260–4240 | |
| | Density | 6980–4240 | 4018–1567, 787–658 |
| Decanter (Light Phase) | MeI | 6211–5505 | 2520–2454 |
| | HOAc | 6980–4600 | 1836–1662 |
| | MeOAc | 6210–5505, 4730–4240 | 1836–1662, 1131–991 |
| | $H_2O$ | 6980–6120, 5580–4530 | 3946–2471 |
| | $CH_3CHO$ | 6260–4240 | |
| | Density | 6980–4240 | 3946–2420, 787–658 |
| Light Ends | HI | 4808–4240 | 4038–1787, 1366–1307 |
| | $H_2O$ | 5561–4579 | 4086–2140 |
| Bottoms | HOAc | 6957–5550, 4620–4240 | 4100–1780, 1366–699 |
| Heavy Ends/ Product | $H_2O$ | 5580–4884 | |
| | Propionic Acid | 6700–5590, 4700–4240 | |
| Drying Column Feed | HI | 4808–4240 | |
| | $H_2O$ | 5580–4700 | 4120–2140 |
| | HOAc | 6957–5550, 4610–4240 | 4100–1780, 1366–699 |
| Drying Column | $H_2O$ | 5700–4600 | 4120–2140 |
| | HOAc | 6957–5800, 4610–4240 | 4100–1780, 1366–699 |

Attenuated Total Reflectance (ATR) referred to in the title of Table 1 is a technique well known to those skilled in the art of spectroscopy and involves light from an infrared source entering a crystal made from an infrared transmitting material of high refractive index. The light is internally reflected and extends beyond the surface of the crystal into the sample that is in contact with the crystal. A portion of the infrared energy is absorbed and the remainder of the energy is passed on to a detector. ATR produces a very short pathlength for the infrared light in the sample.

The term transmission used in Table 1 refers to the case where infrared energy is passed directly through a sample, which absorbs a portion of the infrared energy. Similar to the ATR technique, the remainder of the energy reaches the detector.

It is well known to those skilled in the art of infrared spectroscopy that fundamental absorption bands in the mid-infrared have corresponding overtone bands or "echoes" of lower intensity in the extended mid-/near-infrared region. The near-infrared region, which incorporates the extended mid-infrared region, stretches from approximately 4000 $cm^{-1}$ to 12500 $cm^{-1}$. The first overtone bands occurring in the extended mid-infrared region are approximately an order of magnitude less intense than the fundamental absorbances. Similarly, the second overtone bands occurring at even higher near-infrared frequencies are an order of magnitude lower in intensity again. Thus, any of the overtone bands in the near-infrared could be used for quantitative analysis by modifying the cell or probe window pathlength. All bands of interest for the measurement of components according to the invention fall within the infrared region.

The infrared instrument, transmission cells, ATR cell and transmission probe to be described in the laboratory simulations are substantially the same as equipment used in a manufacturing facility. Process hardened versions of laboratory infrared spectrometers are supplied by several vendors such as Analect Instruments, Pomona, CA and ABB Bomem Inc., Quebec, Canada. While the electronic components of laboratory and process spectrometers are essentially identical, safety and environmental considerations require that process spectrometers are packaged in explosion proof, purged cabinets. Similarly, because of changing climatic conditions in a process environment compared to a laboratory, infrared cells are usually maintained at a constant temperature in a conditioned sample cabinet.

It should be understood also that the appropriate spectral region used for quantitatively analyzing a particular component may vary depending on the vessel or stream in which it is being analyzed, given that a particular component may be more concentrated at one location in the reaction system as compared to its concentration at another location. This can be seen in Table 1, where, for example, MeI is measured in the extended mid-infrared region of 6261–5351 $cm^{-1}$ in the decanter heavy phase and in the extended mid-infrared region of 6211–5505 $cm^{-1}$ in the decanter light phase.

For each stream or vessel to be simulated, multi component solutions were prepared to obtain the spectroscopic data necessary to create calibration models. Concentration ranges for these solutions were consistent with the ranges examined in the individual on-line examples detailed within. For example, the concentration ranges used in preparation of decanter light and heavy phase calibration standards are listed below:

| LIGHT PHASE | |
|---|---|
| Water ($H_2O$) | 20–50 molar |
| Acetic Acid (HOAc) | 0–9 molar |
| Methyl Acetate (MeOAc) | 0–4 molar |
| Methyl Iodide (MeI) | 0–3 molar |
| Acetaldehyde ($CH_3CHO$) | 0–20,000 ppm |
| HEAVY PHASE | |
| Water ($H_2O$) | 0–1.5 molar |
| Acetic Acid (HOAc) | 0–3.5 molar |

-continued

| | |
|---|---|
| Methyl Acetate (MeOAc) | 0–4 molar |
| Methyl Iodide (MeI) | 8–15 molar |
| Hydrocarbons | 0–1 molar |
| Acetaldehyde (CH$_3$CHO) | 0–20,000 ppm |

As outlined in the above identified applications, calibration models for all components in all vessels/streams were validated by preparing solutions of known component concentrations, obtaining infrared spectra of these components and quantitatively analyzing these spectra using the appropriate calibration models.

Figure 2:
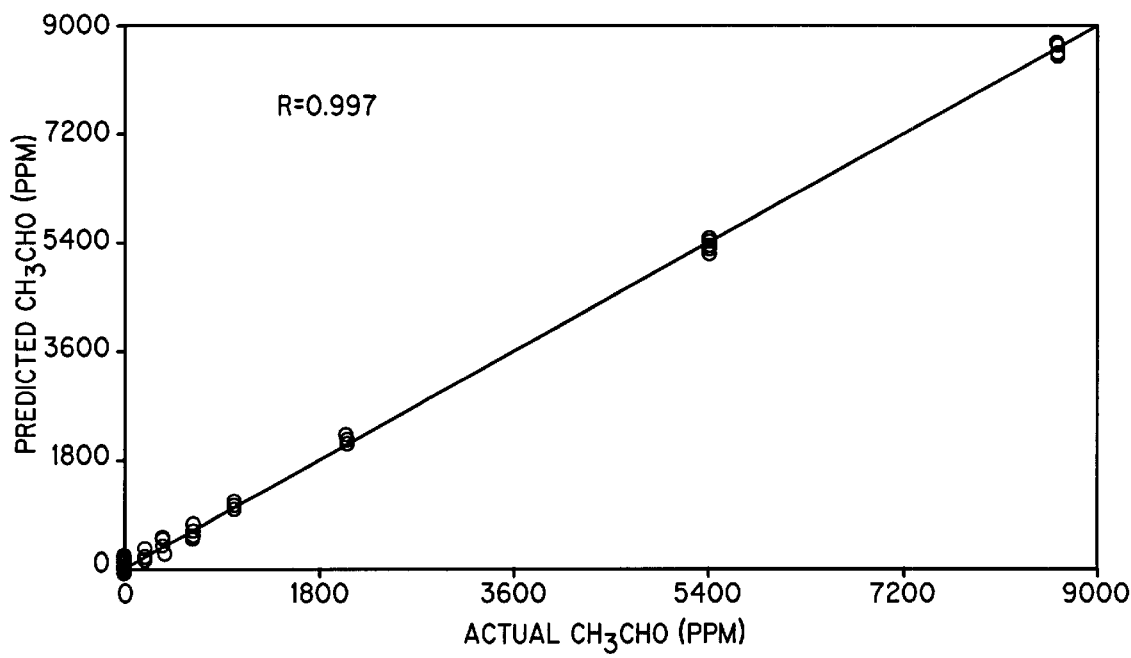
FIG. 2 is a correlation plot of actual vs. predicted concentration values for acetaldehyde ($CH_3CHO$) showing the validation of the laboratory calibration model in the decanter heavy phase.

Validation of the decanter heavy phase calibration models is provided in tabular form in Table 2, and in graphical format for CH$_3$CHO in FIG. 2, in which eight solutions of known composition were prepared and concentrations were predicted using the calibration models. Correlation coefficients (R factors) of 0.997 or greater associated with the values in Table 2 indicate a high degree of accuracy for analysis of all components and also for quantitation of density. Similar validation was carried out for the decanter light phase calibration models. Data for this validation is shown in Table 3. Similarly, Tables 4, 5 and 6 report validation data for light ends column bottoms type solutions, heavy ends column/product tank type solutions and drying column feed type solutions, respectively.

TABLE 2

Accuracy of Laboratory Extended Mid-Infrared Calibration Models for Heavy Phase Solutions
Eight Prepared Samples of Known Composition Were Used

| Sample No. | HOAc (Molarity) | | H$_2$O (Molarity) | | MeOAc (Molarity) | | MeI (Molarity) | | Hydrocarbons (Molarity) | | Density (g/mL) | | CH$_3$CHO (ppm) | |
|---|---|---|---|---|---|---|---|---|---|---|---|---|---|---|
| | Actual | Predict | Actual | Predict | Actual | Predict | Actual | Predict | Actual | Predict | Actual | Predict | Actual | Predict |
| 1 | 1.64 | 1.53 | 0.00 | 0.02 | 0.00 | 0.00 | 14.44 | 14.20 | 0.00 | −0.03 | 2.16 | 2.16 | 0 | 142 |
| 2 | 2.34 | 2.41 | 0.94 | 1.00 | 2.01 | 2.05 | 9.58 | 9.79 | 0.50 | 0.46 | 2.01 | 2.02 | 8600 | 8486 |
| 3 | 2.24 | 2.23 | 0.52 | 0.54 | 0.83 | 0.87 | 11.94 | 12.02 | 0.28 | 0.25 | 1.95 | 1.95 | 635 | 571 |
| 4 | 1.01 | 0.98 | 0.04 | 0.06 | 0.40 | 0.39 | 14.11 | 13.96 | 0.14 | 0.13 | 2.13 | 2.13 | 356 | 432 |
| 5 | 0.00 | −0.02 | 0.09 | 0.08 | 1.47 | 1.51 | 13.09 | 13.17 | 0.34 | 0.35 | 2.02 | 2.03 | 0 | 95 |
| 6 | 3.11 | 3.08 | 0.39 | 0.41 | 2.87 | 2.87 | 9.19 | 9.33 | 0.06 | 0.05 | 1.73 | 1.73 | 5405 | 5350 |
| 7 | 0.21 | 0.21 | 0.00 | 0.03 | 0.20 | 0.19 | 15.30 | 15.12 | 0.03 | 0.03 | 2.23 | 2.22 | 201 | 275 |
| 8 | 2.55 | 2.61 | 1.04 | 1.08 | 2.88 | 2.93 | 6.94 | 7.11 | 0.92 | 0.85 | 1.58 | 1.60 | 2034 | 2159 |

TABLE 3

Accuracy of Laboratory Extended Mid-Infrared Calibration Models for Light Phase Solutions
Eight Prepared Samples of Known Composition Were Used

| Sample No. | HOAc (Molarity) | | H$_2$O (Molarity) | | MeOAc (Molarity) | | MeI (Molarity) | | Density (g/mL) | | CH$_3$CHO (ppm) | |
|---|---|---|---|---|---|---|---|---|---|---|---|---|
| | Actual | Predict | Actual | Predict | Actual | Predict | Actual | Predict | Actual | Predict | Actual | Predict |
| 1 | 6.07 | 5.97 | 25.26 | 25.24 | 2.12 | 2.08 | 0.51 | 0.54 | 1.05 | 1.05 | 2146 | 2229 |
| 2 | 8.03 | 8.11 | 22.95 | 23.08 | 1.07 | 1.06 | 0.69 | 0.71 | 1.07 | 1.08 | 0 | 124 |
| 3 | 0.00 | 0.01 | 45.48 | 45.41 | 2.45 | 2.35 | 0.00 | 0.04 | 0.99 | 1.00 | 620 | 688 |
| 4 | 3.63 | 3.54 | 37.17 | 37.21 | 1.37 | 1.36 | 0.25 | 0.23 | 1.02 | 1.03 | 210 | 302 |
| 5 | 3.98 | 3.86 | 42.35 | 42.94 | 0.00 | −0.02 | 0.15 | 0.12 | 1.02 | 1.03 | 1254 | 1198 |
| 6 | 8.84 | 8.86 | 23.85 | 24.00 | 0.24 | 0.21 | 0.74 | 0.74 | 1.08 | 1.09 | 412 | 516 |
| 7 | 6.97 | 7.08 | 13.67 | 13.70 | 3.61 | 3.66 | 1.14 | 1.08 | 1.10 | 1.11 | 8168 | 8334 |
| 8 | 1.67 | 1.52 | 48.07 | 48.20 | 0.46 | 0.43 | 0.00 | 0.03 | 1.03 | 1.03 | 4692 | 4614 |

TABLE 4

Accuracy of Laboratory Infrared Calibration Models for Light Ends Column Bottoms Solutions
Comparison of Extended Mid (0.5 mm Transmission Cell) and Mid (ATR Cell)
Eight Prepared Samples of Known Composition Were Used

| Sample No. | H$_2$O (Molarity) | | | HI (Molarity) | | | HOAc (Molarity) | | |
|---|---|---|---|---|---|---|---|---|---|
| | Actual | Predict Ext. Mid | Predict ATR | Actual | Predict Ext. Mid | Predict ATR | Actual | Predict Ext. Mid | Predict ATR |
| 1 | 3.69 | 3.70 | 3.65 | 0.086 | 0.091 | 0.079 | 16.27 | 16.24 | 16.29 |
| 2 | 4.44 | 4.44 | 4.41 | 0.14 | 0.15 | 0.15 | 16.01 | 15.97 | 16.00 |
| 3 | 5.79 | 5.76 | 5.82 | 0.018 | 0.018 | 0.017 | 15.66 | 15.62 | 15.67 |
| 4 | 6.62 | 6.62 | 6.66 | 0.20 | 0.21 | 0.19 | 15.29 | 15.25 | 15.31 |
| 5 | 7.28 | 7.30 | 7.29 | 0.30 | 0.29 | 0.30 | 15.03 | 14.98 | 15.03 |
| 6 | 9.66 | 9.68 | 9.57 | 0.031 | 0.034 | 0.033 | 14.45 | 14.41 | 14.44 |
| 7 | 8.44 | 8.46 | 8.48 | 0 | 0.003 | 0.002 | 14.84 | 14.80 | 14.84 |
| 8 | 4.44 | 4.44 | 4.45 | 0 | 0.004 | 0.002 | 16.09 | 16.04 | 16.08 |

TABLE 5

Accuracy of Laboratory Extended Mid-Infrared Calibration Models for Propionic Acid and $H_2O$ in Heavy Ends Column Feed and in Product Tank Feed Solutions
Eight Prepared Samples of Known Composition Were Used

| Sample No. | $H_2O$ (ppm) | | Propionic Acid (ppm) | |
| --- | --- | --- | --- | --- |
| | Actual | Predict | Actual | Predict |
| 1 | 486 | 451 | 105 | 34 |
| 2 | 486 | 464 | 2490 | 2384 |
| 3 | 542 | 530 | 562 | 620 |
| 4 | 668 | 679 | 1584 | 1514 |
| 5 | 734 | 719 | 388 | 426 |
| 6 | 819 | 836 | 970 | 1010 |
| 7 | 936 | 952 | 105 | 164 |
| 8 | 1174 | 1149 | 224 | 264 |

TABLE 6

Accuracy of Laboratory Extended Mid-Infrared Calibration Models for HI in Drying Column Feed Solutions Eight Prepared Samples of Known Composition Were Used

| | HI (ppm) | |
| --- | --- | --- |
| Sample No. | Actual | Predict |
| 1 | 0 | 63 |
| 2 | 121 | 94 |
| 3 | 246 | 292 |
| 4 | 383 | 339 |
| 5 | 479 | 432 |
| 6 | 604 | 648 |
| 7 | 921 | 954 |
| 8 | 2028 | 2069 |

The interchangeability of the ATR method and the extended-mid transmission infrared method of analysis is illustrated by the two sets of data in Table 4. This table compares the accuracy of the ATR method versus the extended mid transmission method for analysis of light ends column bottoms type solutions. The table shows excellent accuracy for both techniques over all ranges of HI, $H_2O$ and HOAc examined.

The accuracy and precision of an infrared measurement are largely a function of the signal to noise ratio for the spectral response of the component of interest. Noise refers to small, random variations in instrument performance usually associated with electronics. It is well known to those skilled in the art of spectroscopy that when the component being measured is present in sufficiently high concentration the signal to noise ratio is very large and noise will not adversely affect quantitation. When the infrared signal is very small, as in the measurement of ppm levels of acetaldehyde in both decanter phases and in the measurement of ppm levels of propionic acid in heavy ends column or product stream solutions, the signal to noise ratio can be sufficiently low such that the noise impacts quantitation. This random contribution of noise can be averaged out by:

(a) increasing the length of time to acquire a spectrum. A typical acquisition time is of the order of 30 seconds. Increasing this to 1–3 minutes, for example, will dampen the noise while leaving the signal unaffected; or (b) averaging the results for a number of spectra and reporting the average. Both of these averaging techniques were used in acquisition of quantitative data for ppm levels of acetaldehyde, HI, water and propionic acid. The correlation plot in FIG. 2 shows the scatter associated with five repeat measurements for decanter heavy phase acetaldehyde in each of the eight validation solutions. At concentrations below 1000 ppm, individual predicted values may vary by as much as +/−300 ppm from the actual value. However, the average of 5 measurements which is the value reported in Table 2, improves the accuracy to about +/−100 ppm. Even with this averaging, the signal is too low to allow reliable quantitation at concentrations below 200 ppm acetaldehyde. Similarly, ppm values of propionic acid and water in Table 5 and ppm values of HI in Table 6 are the average of 5 measurements. It should be noted, however, that the infrared measurements of individual components will vary in accuracy and precision as a function of the particular mixture of components in the sample. Thus, where a particular spectral response is strong and distinguishable from responses due to other components in a sample, good signal to noise ratios are obtained even though the concentration of the component may be low. Thus, although the concentrations of water as reported in Table 5 have low ppm values, water tends to have a more intense and distinct signal, resulting in greater reliability and less variance between actual and predicted values, as compared to the other low ppm concentration components.

EXAMPLES

Figure 3:
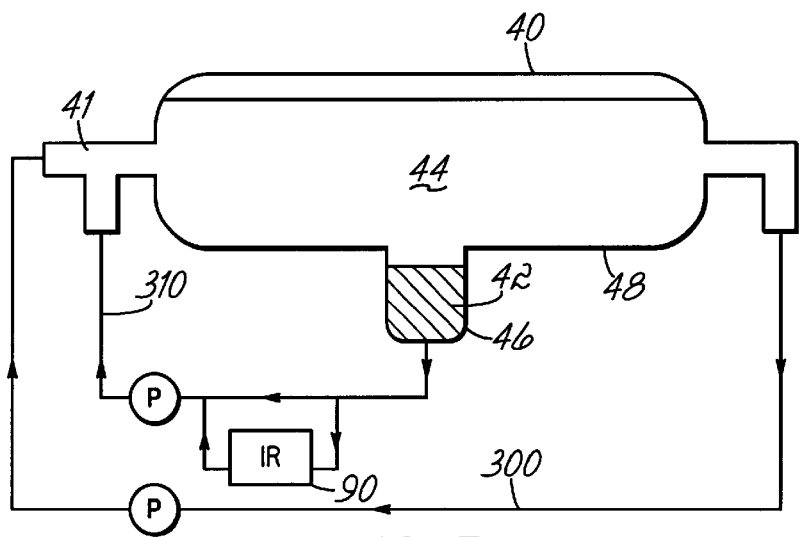
FIG. 3 is a schematic representation of one mode of the on-line analysis of the present invention in the decanter of the light ends recovery section.

In all examples relating to the decanter 40, equipment as shown in FIG. 3 was used to simulate the process equipment. A glass decanter 40, made from a glass reducing Tee, was used to study the appearance and measure the compositions of the light phase 44 and heavy phase 42. The dimensions of the main section 48 of the decanter 40 were 3 inches inner diameter by 14 inches long, and the boot 46 was 2 inches inner diameter by 5 inches long. Typical light and heavy phase compositions were prepared and added to the decanter 40. The heavy phase 42 collected in the bottom of boot section 46, with an interface about 2 inches below the bottom level of the main section 48 of the decanter 40. To minimize the material for these studies, the light phase 44 and heavy phase 42 were independently and continuously recirculated via return lines 300, 310 respectively, with pumps P back to the decanter main section 48. The two streams from the return lines 300, 310 were mixed with a static mixer 41 just before entering the decanter 40 to simulate the mixture of components that is typically experienced in a commercial or pilot plant. In this manner, compositional equilibrium could be established between the light phase 44 and heavy phase 42. Composition was changed by adding additional water, acetic acid, methyl acetate, hydrocarbons, MeI, $CH_3CHO$ or mixtures thereof to the light phase 44. These additions were achieved by means of a three way valve (not shown) connected to the light phase pump inlet (not shown).

Figure 4A:
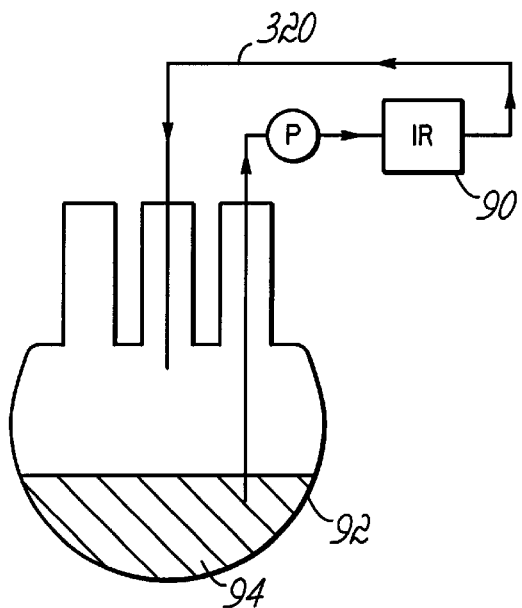
FIG. 4A is a schematic representation of one mode of the on-line analysis of the present invention applicable in the light ends column bottoms, drying column feed, drying column, heavy ends column feed and product tank feed.
Figure 4B:
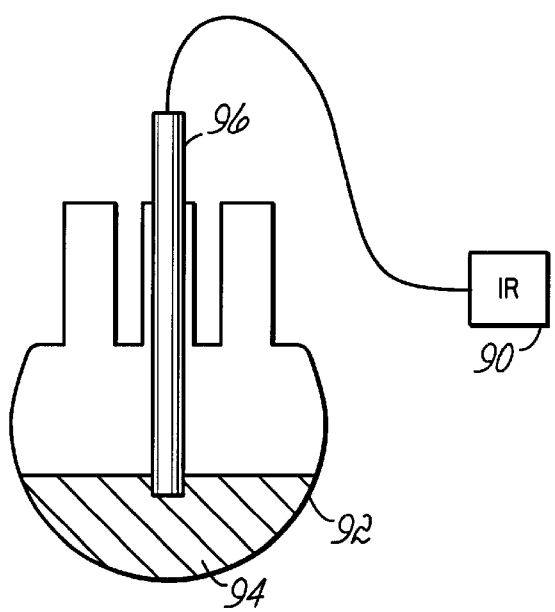
FIG. 4B is a schematic representation of another mode of the on-line analysis of the present invention applicable in the light ends column bottoms, drying column feed, drying column, heavy ends column feed and product tank feed.

In all examples relating to the light ends column 30, drying column 50, heavy ends column 60 and product tank, equipment as shown in FIG. 4A and FIG. 4B was used. A one liter 3 necked round bottomed flask 92 was filled with 300 mL of the appropriate solution 94 and stirred. Compositions were changed by adding the desired component via syringe directly into the flask 92.

In all examples, the principal methods used to analyze manually obtained samples were gas chromatography (GC), Karl Fischer (KF) water titration and argentometric iodide titration. These are well established analytical methods in acetic acid manufacturing with accuracies greater than or equal to +/−5%. GC analyses were carried out using a Varian Instruments, Walnut Creek, Calif. model 3400 instrument, equipped with a NUKOL® 60 meter capillary column and a flame ionization detector. Karl Fischer water analyses were carried out using an EM Sciences, Gibbstown, N.J. AQUASTAR® model V1B titrator. Iodide (as hydriodic acid) analyses were carried out by titration with silver nitrate in which the end-point was determined by use of Eosin Y indicator. Solution densities were determined by weighing 1 mL of solution.

The infrared spectrometer used in all examples was a DIAMOND® 20 model obtained from Analect Instruments, Pomona, Calif. Two types of detector were used. In Examples 1–12, which involved use of a flow through transmission cell mounted in the cell compartment of the spectrometer, a deutero triglycine sulfide (DTGS) detector was used. In all other examples involving use of a fiber optic coupled transmission probe, an indium arsenide (InAs) detector was used. Loss of signal as it is transmitted through fiber optic cables is offset by use of the more sensitive InAs detector.

Figure 5:
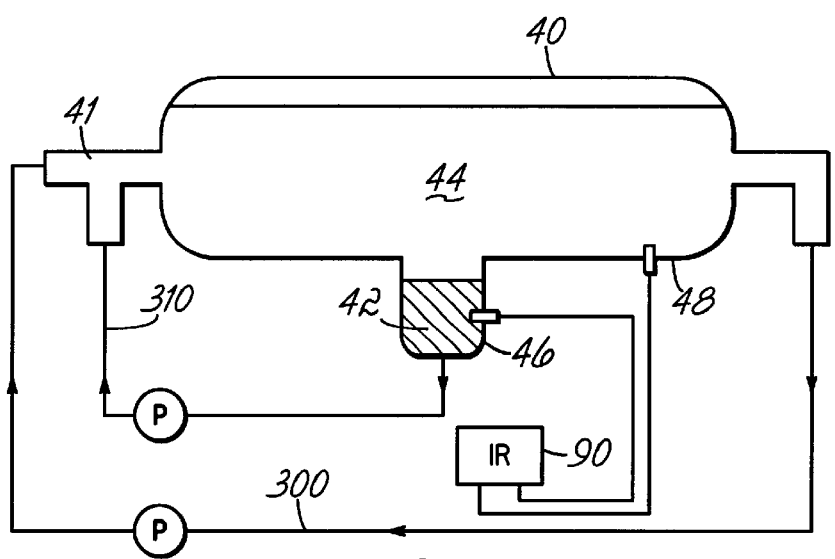
FIG. 5 is a schematic representation of a mother mode of the on-line analysis of the present invention in the decanter of the light ends recovery section.

A number of methods were employed to obtain on-line infrared analysis for testing purposes. Infrared analysis in the extended mid-infrared region for the decanter light phase 44 and heavy phase 42 was carried out by connecting the return line of one of the streams 300, 310 to the inlet of a 0.5 mm transmission cell equipped with zinc selenide windows placed in the cell compartment of an FTIR spectrometer 90, and the outlet was connected to the pump P, which then continuously recirculated the material to the decanter 40, as shown in FIG. 3. Alternatively, a 0.5 mm pathlength fiber optic coupled transmission probe equipped with sapphire windows, obtainable from Axiom Analytical, Irvine, Calif., could be inserted into the main section 48 and boot 46 of the decanter itself, as shown in FIG. 5, or into the return lines 300, 310 (not shown). On-line analyses of solutions in the one liter flask 92 were similarly achieved by continuously circulating the solution 94 via line 320 through the infrared cell 90 back into the flask 92, as shown in FIG. 4A or by direct insertion of the fiber optic coupled transmission probe 96 into the one liter flask 92 as shown in FIG. 4B.

Infrared analyses in the mid-infrared region were similarly carried out by connecting the return line of one of the decanter streams 300, 310 or the outlet line 320 of the flask 92 to the inlet of an ATR tunnel cell equipped with a zinc selenide crystal, obtainable from Axiom Analytical, placed in the compartment of an FTIR spectrometer 90, and the outlet was connected to the pump as described above.

Example 1

Figure 6:
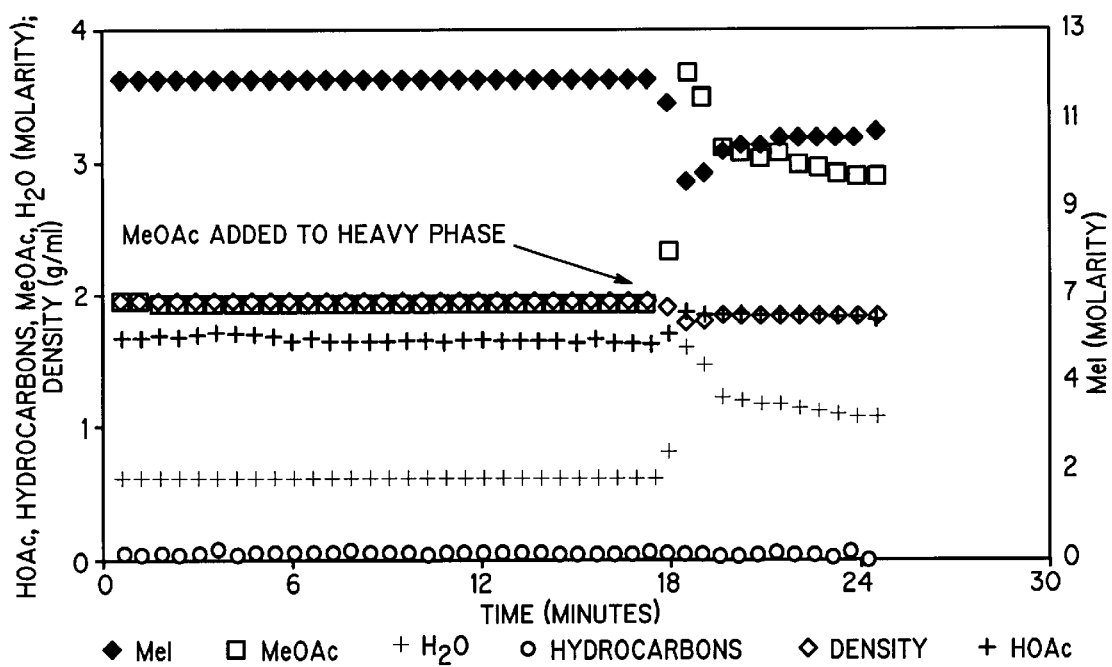
FIG. 6 is a multi-component trend file containing 30 minutes of run time data for five heavy phase decanter solution components and solution density.

In this example, the return line 310 of the decanter heavy phase solution was connected to a 0.5 mm transmission cell equipped with zinc selenide windows, i.e. the heavy phase 42 was continuously monitored by extended mid-infrared analysis. The transmission cell was placed in the cell compartment of an FTIR spectrometer equipped with a DTGS detector. Decanter solution of composition as shown in the first data column of Table 7 was allowed to circulate for about 18 minutes while an on-line data point was being recorded about every 35 seconds, as shown in FIG. 6. The trend lines for this 18 minute period show that a measurement precision of better than +/−0.06 molar was achieved for all components. At this point MeOAc was added to the decanter. The trend lines in FIG. 6 show the effect of this MeOAc addition on heavy phase composition as measured by infrared. As expected, MeOAc showed a significant increase in concentration from 2 molar to 2.65 molar and MeI, the bulk solvent in the heavy phase, decreased in concentration from 11.7 molar to 10.7 molar. The presence of a higher concentration of MeOAc in the heavy phase also allowed greater solubility of both HOAc and water as shown by the trend lines.

The heavy phase was manually sampled before and after the MeOAc addition. These samples were analyzed by off-line independent methods of analysis, specifically GC and Karl Fischer. The data in Table 7 show excellent agreement between the values predicted by on-line infrared and the off-line techniques and illustrate the ability of on-line line infrared analysis to detect even small changes in component concentrations brought about by increasing concentration of MeOAc in the heavy phase.

TABLE 7

Addition of MeOAc to Decanter Heavy Phase
Correlation of On-Line Extended Mid-Infrared Values with Independent Off-Line Analytical Techniques (GC/Karl Fischer)

| Component | On-Line Infrared | | GC | | Karl Fischer | |
| --- | --- | --- | --- | --- | --- | --- |
| | Before Addition | After Addition | Before Addition | After Addition | Before Addition | After Addition |
| $H_2O$ (Molarity) | 0.57 | 0.89 | — | — | 0.59 | 0.93 |
| HOAc (Molarity) | 1.45 | 1.63 | 1.47 | 1.56 | — | — |
| MeOAc (Molarity) | 1.98 | 2.65 | 1.95 | 2.79 | — | — |
| MeI (Molarity) | 11.72 | 10.71 | 11.80 | 10.63 | — | — |
| Hydrocarbons (Molarity) | 0.069 | 0.072 | 0.045 | 0.042 | — | — |
| Density (g/mL) | 1.95 | 1.86 | 1.96 | 1.85 | — | — |

Example 2

Figure 7:
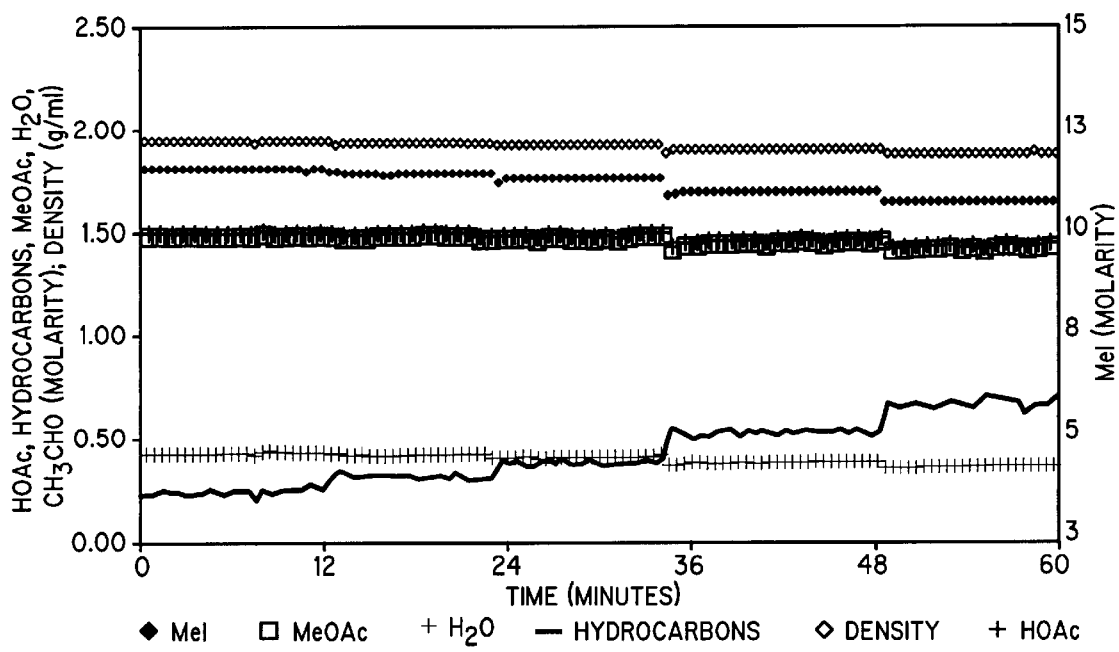
FIG. 7 is a multi-component trend file containing 60 minutes of run time data for five heavy phase decanter solution components and solution density.

Similar conditions to Example 1 were used. A decanter heavy phase solution of composition as shown in the first data row of Table 8 was monitored for a one hour period during which time aliquots of a hydrocarbons solution were added at approximately 12 minute intervals. The trend lines in FIG. 7 show the expected increases in hydrocarbons concentration from about 0.25 molar to about 0.70 molar, coupled with decreases in concentration of other heavy phase components as dilution occurs. Solution density also decreases as a function of the very light hydrocarbons (approximately 0.7 g/mL) replacing the very heavy MeI (approximately 2.3 g/mL). The solution was manually sampled before each hydrocarbons addition and the samples analyzed by off-line independent methods of analysis, specifically GC for concentrations and weighing for density. The data in Table 8 show very close agreement between on-line and off-line techniques and illustrates the ability of on-line infrared to detect and accurately quantify changes in hydrocarbons concentration.

TABLE 8

Addition of Hydrocarbons to Decanter Heavy Phase
Correlation of On-Line Extended Mid-Infrared Values with Independent Off-Line Analytical Techniques (GC/Weighing)

| Hydrocarbons (Molarity) | | HOAc (Molarity) | | H$_2$O (Molarity) | | MeOAc (Molarity) | | MeI (Molarity) | | Density (g/mL) | |
|---|---|---|---|---|---|---|---|---|---|---|---|
| Infrared | GC | Infrared | GC | Infrared | GC | Infrared | GC | Infrared | GC | Infrared | Weighing |
| 0.24 | 0.27 | 1.52 | 1.58 | 0.43 | 0.45 | 1.49 | 1.43 | 11.82 | 11.91 | 1.97 | 1.98 |
| 0.32 | 0.33 | 1.50 | 1.55 | 0.42 | 0.42 | 1.48 | 1.43 | 11.66 | 11.69 | 1.96 | 1.96 |
| 0.37 | 0.40 | 1.47 | 1.49 | 0.40 | 0.39 | 1.46 | 1.40 | 11.50 | 11.45 | 1.94 | 1.94 |
| 0.53 | 0.55 | 1.44 | 1.42 | 0.37 | 0.36 | 1.43 | 1.38 | 11.18 | 11.21 | 1.91 | 1.90 |
| 0.67 | 0.70 | 1.40 | 1.38 | 0.35 | 0.33 | 1.40 | 1.34 | 10.91 | 10.96 | 1.88 | 1.87 |

Example 3

Figure 8:
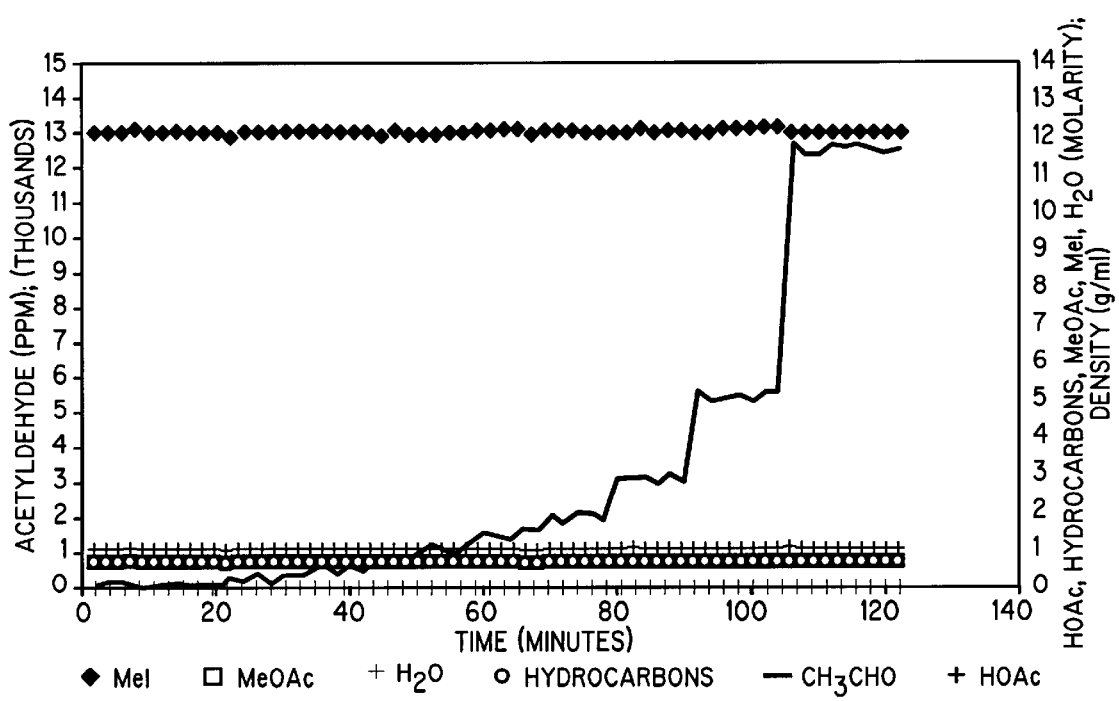
FIG. 8 is a multi-component trend file containing 140 minutes of run time data for six heavy phase decanter solution components.

Similar conditions to Example 1 were used except where noted. This example demonstrates on-line monitoring of acetaldehyde as its concentration increases in the decanter heavy phase. A heavy phase solution was monitored for a 2 hour period during which time a data point was obtained every 2 minutes. During this 2 hour period, 9 aliquots of acetaldehyde were added. The trend lines in FIG. 8 show the increase in acetaldehyde from a starting value of zero up to about 12,000 ppm. The solution was manually sampled before each acetaldehyde addition and the samples analyzed by GC. Because of residual noise present in the infrared data, five infrared data points were averaged to give the infrared data in each row of Table 9. As shown in this table, data point averaging allows an accuracy of approximately +/-150 ppm when the infrared values are compared to the GC values. This example thus shows that using a rolling average of data points over a reasonably brief time period, such as about 10 minutes allows effective monitoring of acetaldehyde at levels normally expected in decanter heavy phase operation.

TABLE 9

Addition to Acetaldehyde to Decanter Heavy Phase
Correlation of On-Line Extended Mid-Infrared Values with Independent Off-Line Analytical Techniques (GC)

| Infrared (ppm) | GC (ppm) |
|---|---|
| 69 | 0 |
| 306 | 258 |
| 421 | 515 |
| 710 | 773 |
| 1149 | 1031 |
| 1586 | 1489 |

TABLE 9-continued

Addition to Acetaldehyde to Decanter Heavy Phase
Correlation of On-Line Extended Mid-Infrared Values with Independent Off-Line Analytical Techniques (GC)

| Infrared (ppm) | GC (ppm) |
|---|---|
| 1884 | 1946 |
| 3120 | 3095 |
| 5552 | 5447 |
| 12317 | 12115 |

Example 4

Figure 9:
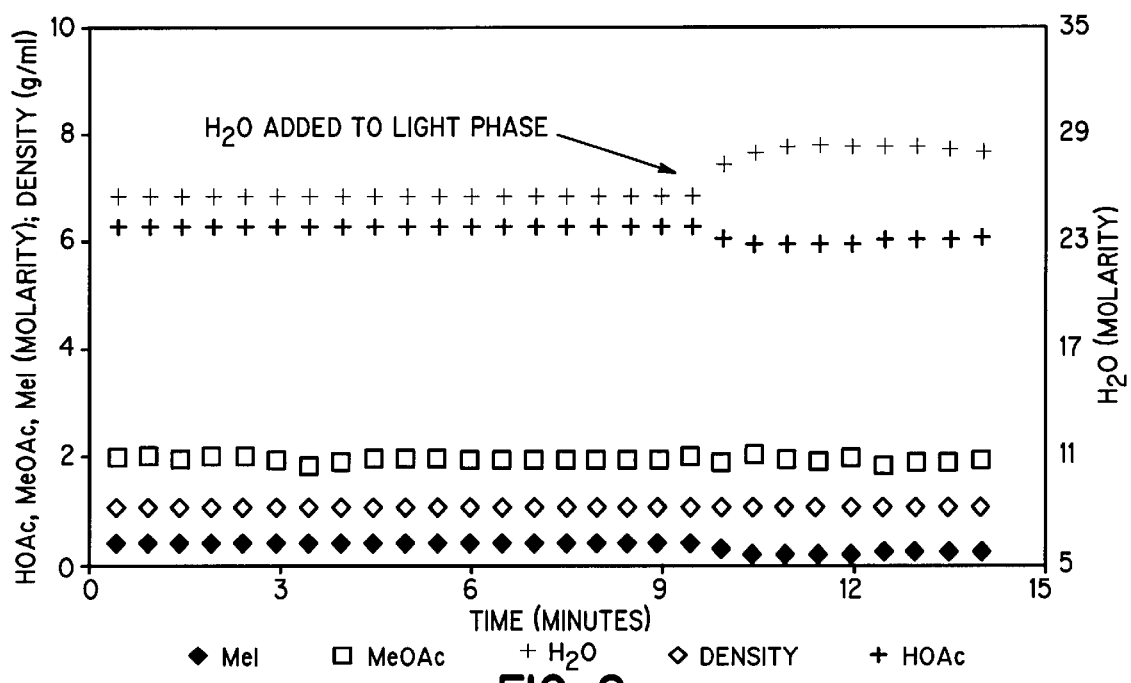
FIG. 9 is a multi-component trend file containing 15 minutes of run time data for four light phase decanter solution components and solution density.

In this example, the return line 300 of the decanter light phase 44 was connected to the infrared cell. Infrared equipment was identical to that described in Example 1. Decanter solution of composition as shown in Table 10 was allowed to circulate for about 9 minutes while an on line data point was being recorded about every 35 seconds, as shown in FIG. 9. The trend lines for this period show that a precision of +/-0.05 molar was achieved for all components. At this point water was added to the decanter. The trends in FIG. 9 show the effect of this water addition on light phase composition as measured by infrared. As expected, water showed a significant increase in concentration from 25.41 molar to 27.92 molar and MeI which is immiscible with water showed the largest percentage decrease in concentration. The light phase was manually sampled before and after water addition and the samples were analyzed by GC and Karl Fischer titration. The data in Table 10 show excellent correlation between on-line infrared and the off-line techniques and demonstrates the ability of on-line infrared to accurately quantify changes in light phase solution components in response to changes in water concentration.

TABLE 10

Addition of H$_2$O to Decanter Heavy Phase
Correlation of On-Line Extended Mid-Infrared Values with Independent Off-Line Analytical Techniques (GC/Karl Fischer)

| Component | On-Line Infrared | | GC | | Karl Fischer | |
|---|---|---|---|---|---|---|
| | Before Addition | After Addition | Before Addition | After Addition | Before Addition | After Addition |
| H$_2$O (Molarity) | 25.41 | 27.92 | — | — | 25.35 | 27.86 |
| HOAc (Molarity) | 6.28 | 6.00 | 6.33 | 5.99 | — | — |

TABLE 10-continued

Addition of H₂O to Decanter Heavy Phase
Correlation of On-Line Extended Mid-Infrared Values with Independent Off-Line
Analytical Techniques (GC/Karl Fischer)

| Component | On-Line Infrared | | GC | | Karl Fischer | |
|---|---|---|---|---|---|---|
| | Before Addition | After Addition | Before Addition | After Addition | Before Addition | After Addition |
| MeOAc (Molarity) | 1.94 | 1.87 | 1.89 | 1.83 | — | — |
| MeI (Molarity) | 0.40 | 0.26 | 0.42 | 0.26 | — | — |

Example 5

Figure 10:
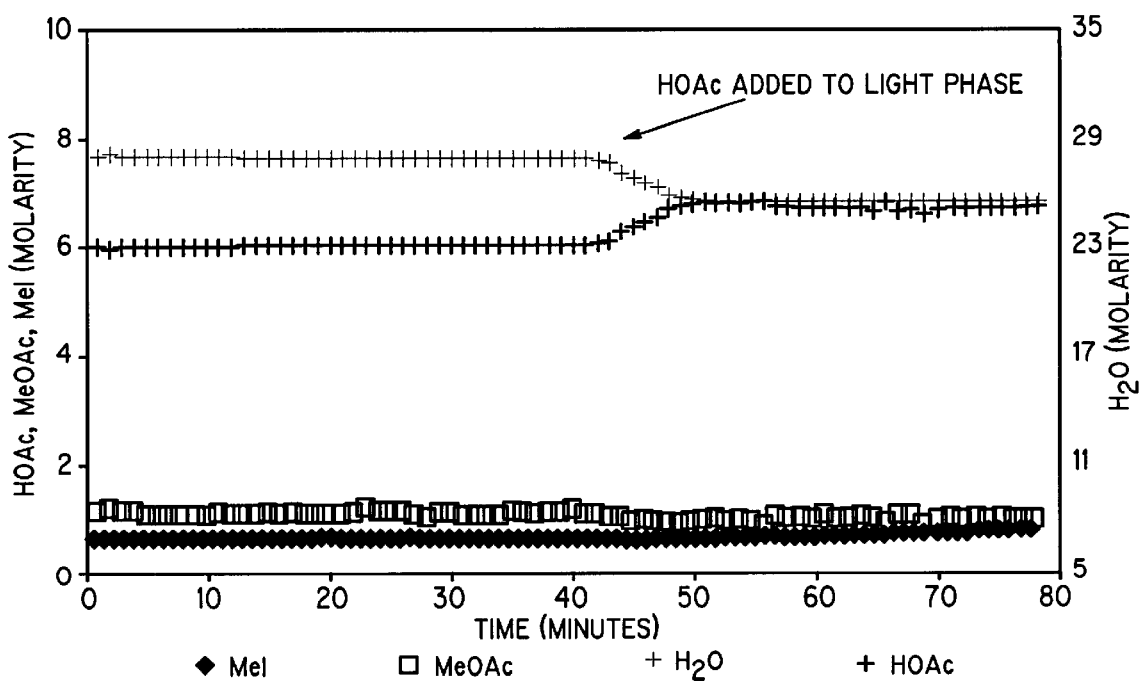
FIG. 10 is a multi-component trend file containing 80 minutes of run time data for four light phase decanter solution components.

This example is similar to Example 4 except that HOAc was added to the decanter instead of water. The trend lines in FIG. 10 show the effect of this HOAc addition on light phase composition. As expected, water, the bulk solvent in the light phase 44 showed a significant decrease in concentration from 28.02 molar to 25.56 molar. The lower water concentration in the light phase 44 led to an increase in MeI concentration in this phase, i.e. a redistribution in MeI from the heavy phase 42 to the light phase 44. The light phase 44 was manually sampled before and after HOAc addition. The data in Table 11 show excellent correlation between the values predicted by on-line infrared and the independent off-line GC and Karl Fischer techniques and demonstrates the ability to detect and quantify changes as low as 0.05 molar in all component concentrations.

TABLE 11

Addition of HOAc to Decanter Light Phase
Correlation of On-Line Extended Mid-Infrared Values with Independent Off-Line
Analytical Techniques (GC/Karl Fischer)

| Component | On-Line Infrared | | GC | | Karl Fischer | |
|---|---|---|---|---|---|---|
| | Before Addition | After Addition | Before Addition | After Addition | Before Addition | After Addition |
| H₂O (Molarity) | 28.02 | 25.56 | — | — | 27.97 | 25.53 |
| HOAc (Molarity) | 6.04 | 6.72 | 5.98 | 6.70 | — | — |
| MeOAc (Molarity) | 1.06 | 1.04 | 1.04 | 1.04 | — | — |
| MeI (Molarity) | 0.67 | 0.78 | 0.64 | 0.74 | — | — |

Example 6

Figure 11:
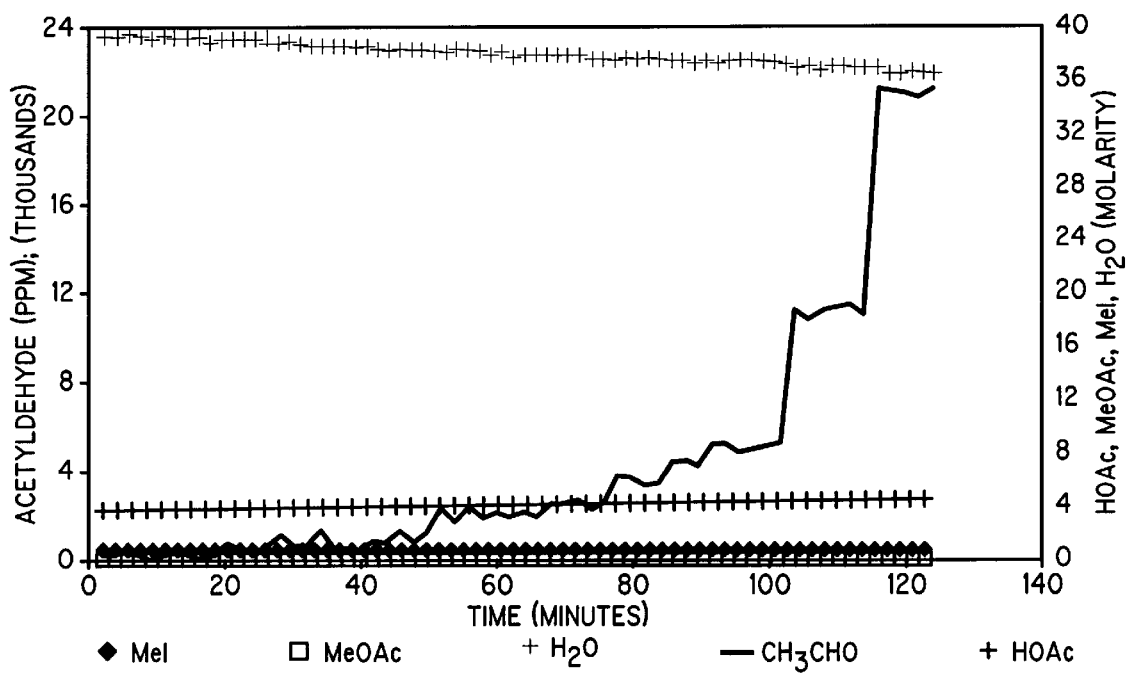
FIG. 11 is a multi-component trend file containing 125 minutes of run time data for five light phase decanter solution components.

Similar conditions to Example 4 were used except where noted. This example demonstrates on-line monitoring of acetaldehyde as its concentration increases in the decanter light phase 44. A light phase solution was monitored for a 2 hour period during which time a data point was obtained every 2 minutes. During this 2 hour period, 10 aliquots of acetaldehyde were added. The trend lines in FIG. 11 show the increase in acetaldehyde from a starting value of zero up to about 21,000 ppm. The solution was manually sampled before each acetaldehyde addition and the samples analyzed by GC. As in Example 3, five infrared data points were averaged to give the infrared data in each row of Table 12. An accuracy of approximately +/−150 ppm is obtained, which demonstrates that using a rolling average of data points over about a 10 minute period allows effective monitoring of acetaldehyde at levels normally expected in decanter light phase operation.

TABLE 12

Addition of Acetaldehyde to Decanter Light Phase
Correlation of On-Line Extended Mid-Infrared Values with
Independent Off-Line Analytical Techniques (GC)

| Infrared (ppm) | GC (ppm) |
|---|---|
| 146 | 0 |
| 259 | 274 |
| 352 | 541 |
| 613 | 752 |
| 1060 | 1021 |
| 1668 | 1581 |
| 1813 | 1952 |
| 3066 | 2946 |
| 4832 | 4787 |
| 11004 | 10839 |
| 20766 | 21093 |

Example 7

Figure 12:
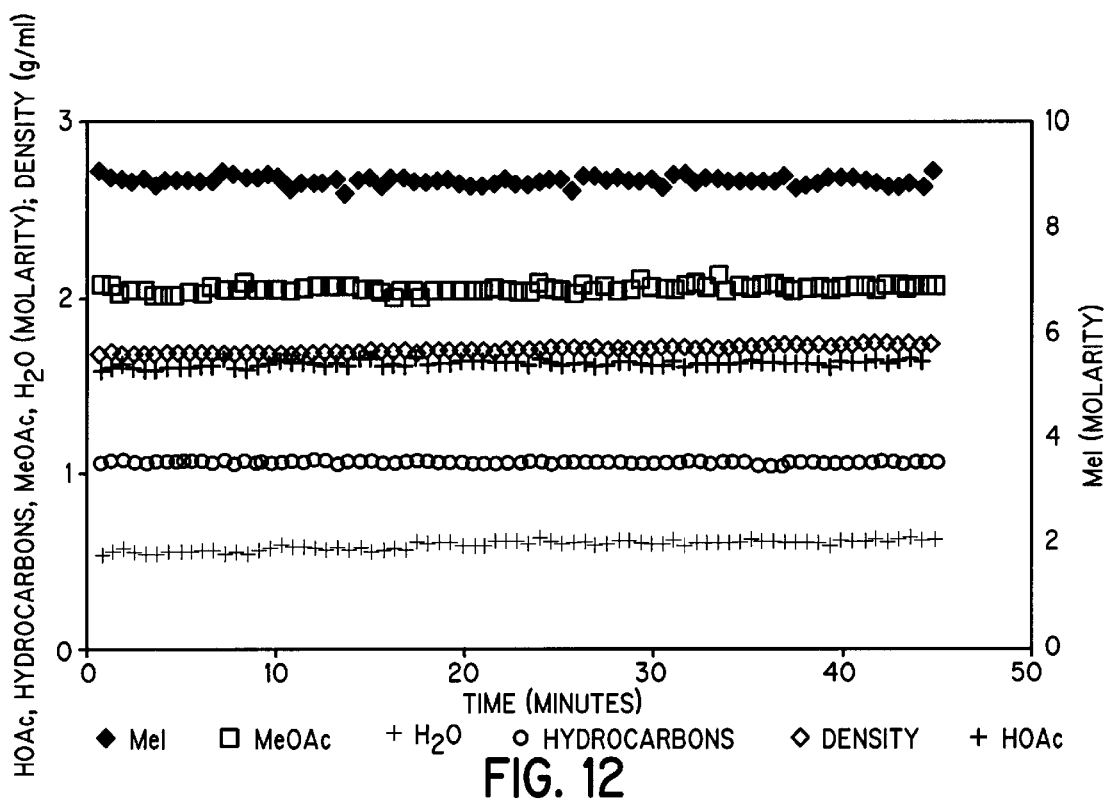
FIG. 12 is multi-component trend file containing 45 minutes of run time data for five light phase decanter solution components and solution density.

In this example the return line 310 from the decanter heavy phase 42 was connected to an ATR tunnel cell equipped with a zinc selenide crystal. Analysis was carried out in the mid infrared region using a DTGS detector. About 45 minutes of on-line data were obtained at a particular fixed decanter composition described in Table 13. A data point acquisition of about 35 seconds was used. A sample obtained at the midpoint of the experiment was analyzed off-line by GC or Karl Fischer and the data compared to on-line data in Table 13. Close agreement between the off-line and on-line values demonstrates the accuracy of the ATR method in on-line analysis. The trend lines in FIG. 12 illustrate the precision of this technique in composition monitoring.

TABLE 13

On-line Analysis of Decanter Heavy Phase Solution in Mid-Infrared Region Using an ATR Cell

| Component | Infrared (Molarity) | GC or KF (Molarity) |
|---|---|---|
| MeI | 8.91 | 8.76 |
| MeOAc | 2.04 | 1.96 |
| HOAc | 1.70 | 1.74 |
| $H_2O$ | 0.59 | 0.55 |
| Hydrocarbons | 1.08 | 1.11 |
| Density | 1.62 | 1.63 |

Example 8

Figure 13:
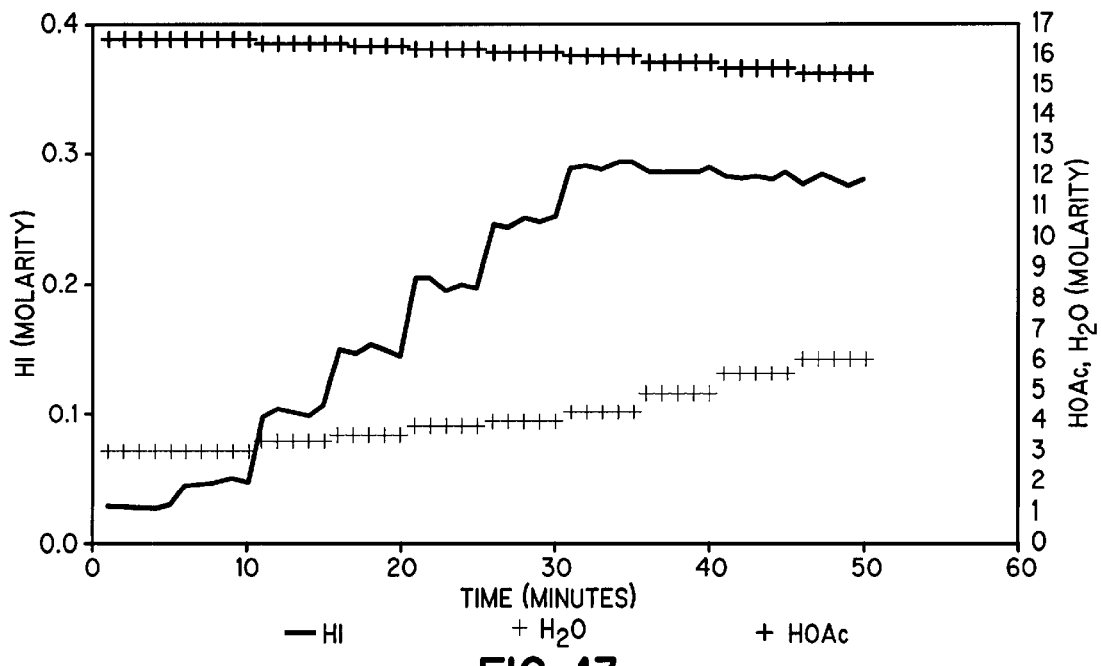
FIG. 13 is a multi-component trend file containing 50 minutes of run time data for three light ends column bottoms solution components.

Using equipment as shown in FIG. 4 and infrared equipment as described in Example 1 (with the exception that sapphire rather than zinc selenide windows were used), a light ends column bottoms 34 type solution was circulated through the infrared transmission cell for 100 minutes. The initial composition of this solution is described in the first row of Table 14. A data point was obtained about every 35 seconds. Over the course of the first 60 minutes, 6 aliquots of HI were added to the flask by syringe. The flask was manually sampled before each HI addition for off-line analysis by titration, GC and Karl Fischer. The trend line plots in FIG. 13 show the stepwise increase in HI after each addition. Water also shows a stepwise addition as the commercial HI used in this experiment is a 55% aqueous solution. To demonstrate that the HI calibration model is not biased or influenced by coincident increase in water, 3 aliquots of water were added during the 60–90 minute period of monitoring. The trend lines show the stepwise increase in water during this period without any increase in HI. HOAc exhibits a steady decrease in concentration over the monitoring period due to dilution with HI/water. Excellent correlation between the off-line analyses and on-line infrared analyses is evident from Table 14. This experiment thus demonstrates the ability of on-line infrared measurement to give a complete and accurate profile of light ends bottoms 34 type solutions. The accuracies of measurement demonstrated in this example show that process control in terms of prevention of azeotropic breakdown could be achieved through on-line infrared analysis.

TABLE 14

Addition of HI and $H_2O$ to Light Ends Bottoms Stream
Correlation of On-Line Extended Mid-Infrared Values with
Independent Off-Line Analysis (GC/Karl Fischer/Titration)

| HI (Molarity) | | $H_2O$ (Molarity) | | HOAc (Molarity) | |
|---|---|---|---|---|---|
| Infrared | Titration | Infrared | KF | Infrared | GC |
| 0.0290 | 0.0294 | 3.01 | 3.07 | 16.51 | 16.52 |
| 0.0471 | 0.0494 | 3.12 | 3.18 | 16.48 | 16.46 |
| 0.102 | 0.101 | 3.39 | 3.45 | 16.37 | 16.35 |
| 0.149 | 0.151 | 3.64 | 3.70 | 16.27 | 16.24 |
| 0.201 | 0.201 | 3.89 | 3.95 | 16.16 | 16.13 |
| 0.248 | 0.249 | 4.12 | 4.18 | 16.05 | 16.02 |
| 0.291 | 0.297 | 4.39 | 4.44 | 15.95 | 15.91 |
| 0.287 | 0.293 | 5.00 | 5.07 | 15.73 | 15.69 |
| 0.282 | 0.290 | 5.62 | 5.71 | 15.54 | 15.47 |
| 0.279 | 0.285 | 6.26 | 6.31 | 15.35 | 15.28 |

Example 9

Figure 14:
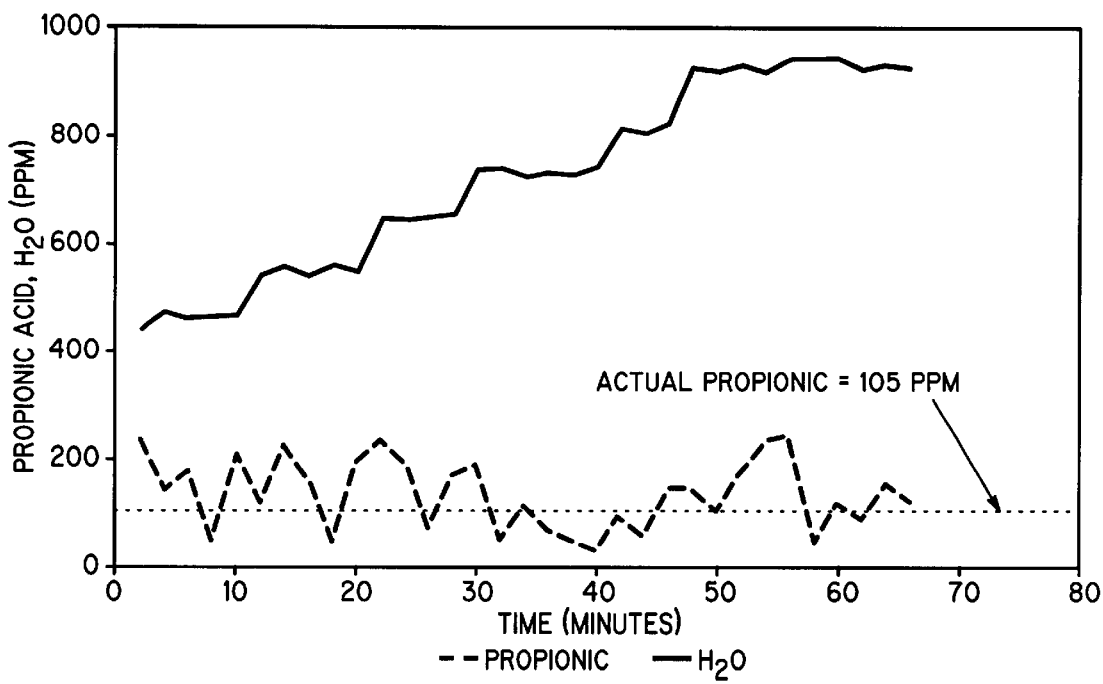
FIG. 14 is a multi-component trend file containing 65 minutes of run time data for two product stream solution components.

Using equipment as in Example 8 and infrared equipment as in Example 1, a product stream 200 type solution was continuously circulated through the infrared transmission cell for about 1 hour. The starting solution was 300 mL of commercial HOAc. It should be noted that all commercially available HOAc contains ppm levels of $H_2O$ and propionic acid. Karl Fischer and GC analysis showed that this starting solution contained 486 ppm $H_2O$ and 105 ppm propionic acid. An infrared data point was obtained every 2 minutes. During the course of monitoring, 5 aliquots of $H_2O$ were added to the flask by syringe. The trend line plot in FIG. 14 shows the increase in $H_2O$ concentration as measured by on-line infrared. Manual samples, obtained before addition of each $H_2O$ aliquot were analyzed by Karl Fischer. Comparison of on-line and off-line data in Table 15 shows that $H_2O$ can be measured with an accuracy of approximately +/−25 ppm. As in Examples 3 and 6, five infrared data points were averaged to obtain the data reported in Table 15. The trend line plot in FIG. 14 also contains data for propionic acid. This plot shows that the variance about the actual value (precision of approximately +/−100 ppm) is uninfluenced by increasing $H_2O$ concentration, i.e., the calibration model for propionic acid is not compromised by variable $H_2O$ in solution. The results from this experiment demonstrate that product quality control in terms of $H_2O$ and propionic acid concentration could be achieved through on-line infrared analysis with a rolling average of data points approximately every 10 minutes.

TABLE 15

Addition of Water to Product Stream
Correlation of On-Line Extended Mid-Infrared
Values with Independent Off-Line Karl Fischer Analysis

| Infrared (ppm) | Karl Fischer (ppm) |
|---|---|
| 460 | 486 |
| 549 | 568 |
| 657 | 650 |
| 721 | 732 |
| 821 | 814 |
| 927 | 913 |

Example 10

Figure 15:
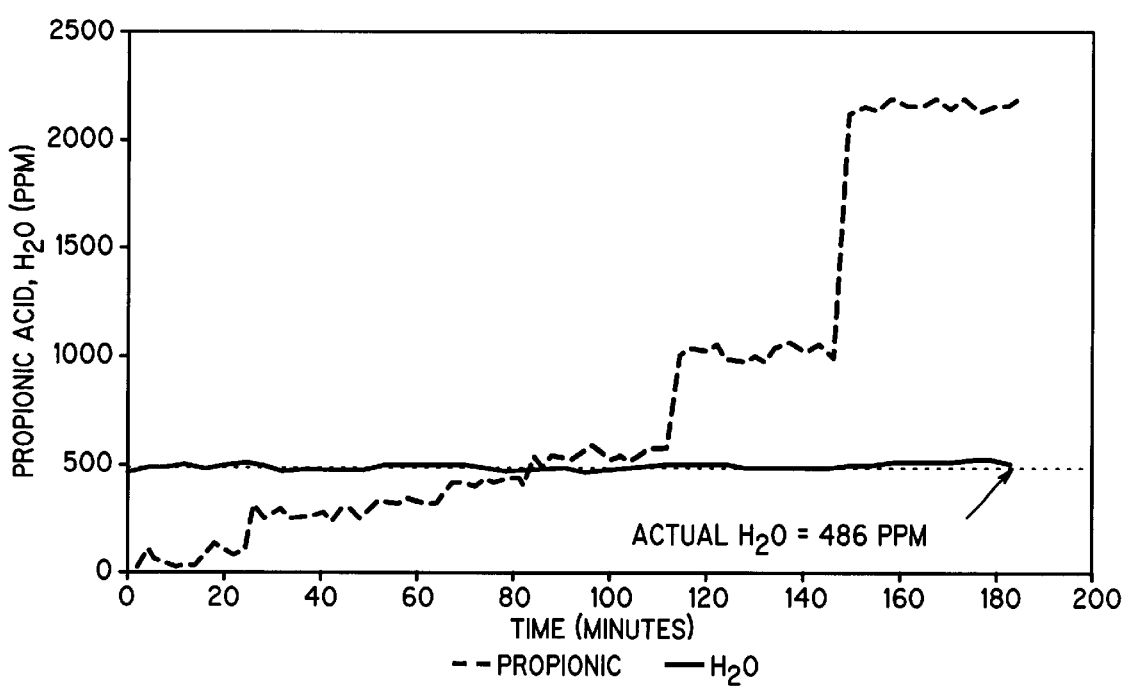
FIG. 15 is a multi-component trend file containing 180 minutes of run time data for two heavy ends column or product stream solution components.

A similar experiment to Example 9 was carried out except that in this case aliquots of propionic acid rather than $H_2O$ were added to HOAc in the flask. The purpose of this experiment was to demonstrate that on-line infrared monitoring of heavy ends column 190 type solutions or product stream 200 type solutions can be used to effectively quantify ppm level changes in propionic acid concentration. Solution was continuously circulated through the infrared cell for 3 hours with a data point frequency of 2 minutes. During this period, 7 aliquots of propionic acid were added via syringe to the flask. The trend line plot in FIG. 15 shows the increase in propionic acid concentration as measured by on-line analysis. Manual samples obtained before every propionic acid addition were analyzed by GC. Comparison of on-line and off-line data in Table 16 in which each reported infrared value is the average of 5 data points, shows that propionic acid can be measured with an accuracy of approximately +/−100 ppm by on-line infrared analysis. This result demonstrates that heavy ends column performance could be monitored and optimized based on the propionic acid concentration in the feed 190 versus propionic acid concentration in the heavy ends flow to a product tank, i.e., product stream 200.

TABLE 16

Addition of Propionic Acid to Product Stream
Correlation of On-Line Extended Mid-Infrared
Values with Independent Off-Line GC Analysis

| Infrared (ppm) | GC (ppm) |
|---|---|
| 45 | 105 |
| 101 | 166 |
| 264 | 218 |
| 308 | 291 |
| 364 | 338 |
| 548 | 527 |
| 1078 | 1149 |
| 2190 | 2038 |

Example 11

Figure 16:
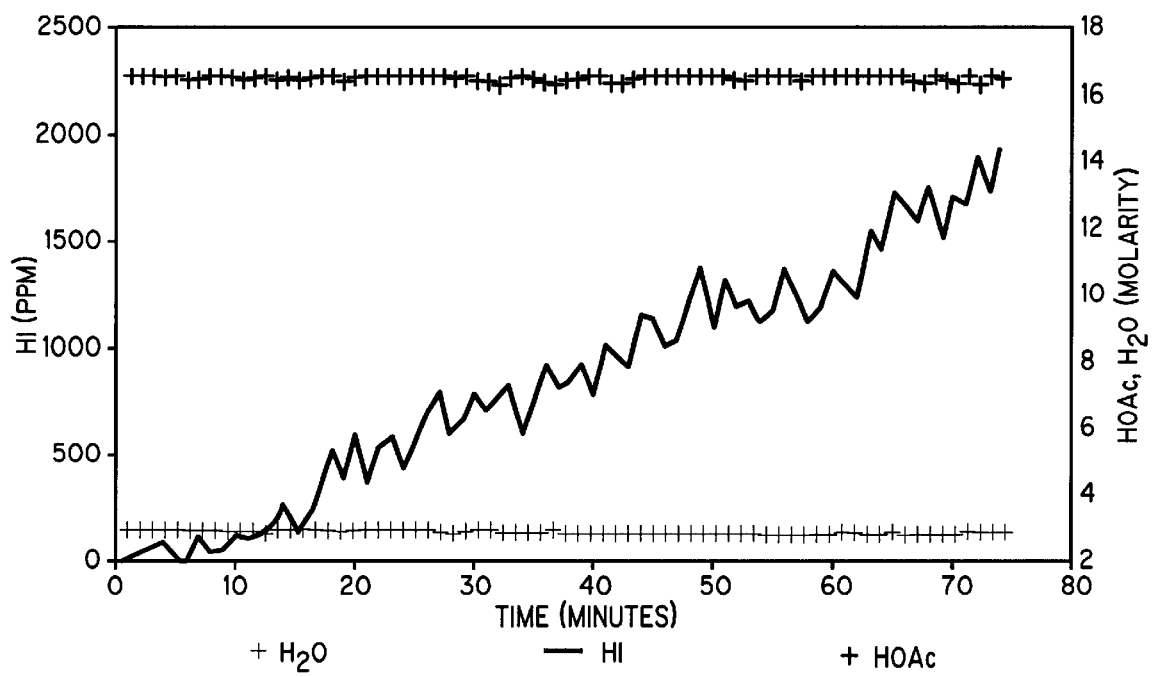
FIG. 16 is a multi-component trend file containing 75 minutes of run time data for three drying column feed components.

Using equipment as shown in FIG. 4 and infrared equipment as described in Example 9, a drying column feed 140 type solution was continuously circulated through the infrared cell for 75 minutes with a data point frequency of 1 minute. The initial composition of this solution was 3.0 molar $H_2O$, 16.6 molar HOAc and zero ppm HI. During the 75 minute period, 15 aliquots of HI solution were added via syringe to the flask. The trend line for HI in FIG. 16 shows the increase in concentration as measured by on-line infrared analysis. Manual samples obtained before every HI addition were analyzed by titration. Comparison of on-line and off-line data in Table 17 in which each reported infrared value is the average of 5 data points, shows that HI can be measured with an accuracy of approximately +/−100 ppm by on-line infrared analysis. Trend lines are also included in FIG. 16 for $H_2O$ concentration and HOAc concentration. Starting and end concentrations as measured by off-line analysis were within 0.05 molar of the on-line infrared values. These results show that monitoring drying column feed 140 by on-line infrared analysis could allow optimization of light ends column performance to minimize HI concentration in this feed. Similarly, measuring the $H_2O$ concentrations in this feed could be used to determine the optimal reflux 170 to the light ends column 30 from the decanter light phase 44.

TABLE 17

Addition of HI to Drying Column Feed
Correlation of On-Line Extended Mid-Infrared
Values with Independent Off-Line Titration Analysis

| Infrared (ppm) | Titration (ppm) |
|---|---|
| 40 | 0 |
| 61 | 106 |
| 136 | 211 |
| 235 | 312 |
| 468 | 422 |
| 525 | 528 |
| 686 | 636 |
| 774 | 744 |
| 830 | 845 |
| 921 | 950 |
| 1053 | 1056 |
| 1188 | 1164 |
| 1224 | 1270 |
| 1387 | 1426 |
| 1614 | 1692 |
| 1825 | 1886 |

Example 12

Figure 17:
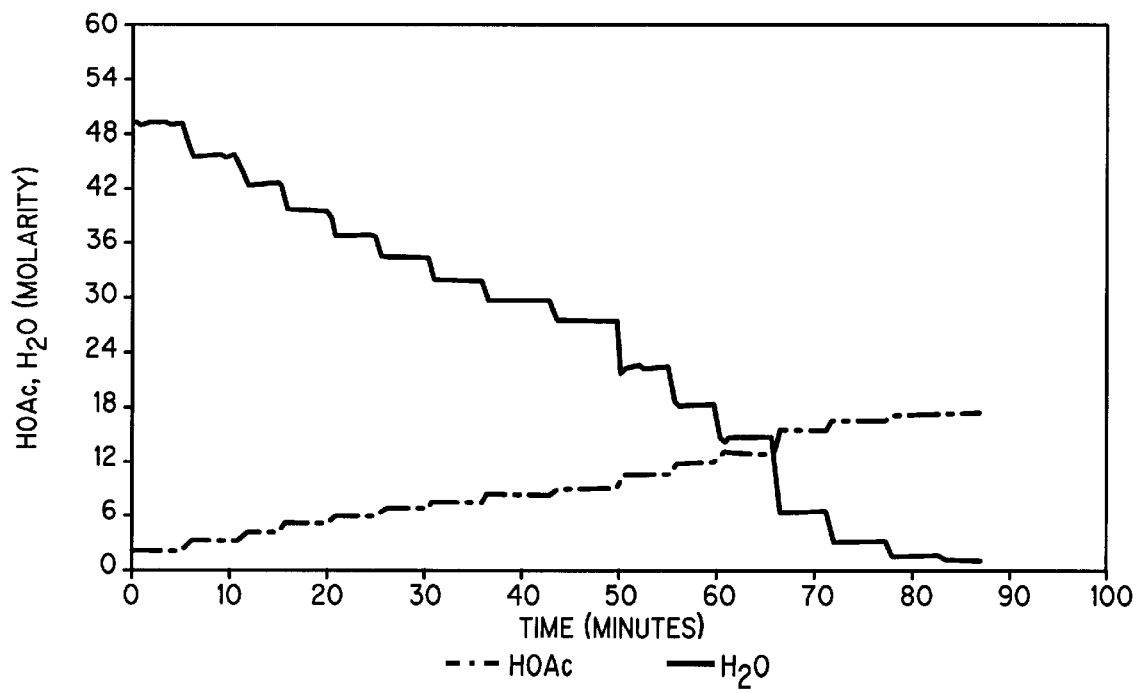
FIG. 17 is a multi-component trend file containing 85 minutes of run time data for two drying column solution components.

Using equipment as shown in FIG. 4 and infrared equipment as described in Example 8, a drying column type solution was continuously circulated through the infrared cell for 85 minutes with a data point frequency of 35 seconds. The initial composition of this solution was 49.3 molar $H_2O$ and 2 molar HOAc. During the 85 minute period of monitoring, 15 aliquots of HOAc were added to the flask via syringe such that the composition changed from almost 100% water on a molar basis to almost 100% HOAc on a molar basis. The trend lines in FIG. 17 show the incremental decreases in $H_2O$ concentration and the corresponding increases in HOAc concentration associated with addition of HOAc aliquots. The purpose of this experiment was to demonstrate that the $H_2O$:HOAc molar ratio, which can vary from 0:100 to 100:0 from the drying column bottoms 52 to the drying column overhead 56 can be measured with great accuracy by on-line infrared. Results in Table 18 show the correlation between off-line analyses by GC and Karl Fischer of manual samples with corresponding on-line infrared values. Both HOAc and $H_2O$ can be measured with an accuracy of+/−0.1 molar over all concentration ranges.

TABLE 18

Addition of HOAc to Drying Column Solution
Correlation of On-Line Extended Mid-Infrared Values
(Transmission Cell) with Independent Off-Line
Analytical Techniques (GC/Karl Fischer)

| $H_2O$ (Molarity) | | HOAc (Molarity) | |
|---|---|---|---|
| Infrared | Karl Fischer | Infrared | GC |
| 49.21 | 49.34 | 2.04 | 2.09 |
| 45.63 | 45.60 | 3.16 | 3.11 |
| 42.57 | 42.68 | 4.07 | 4.18 |
| 39.64 | 39.49 | 5.02 | 4.96 |
| 36.89 | 36.83 | 5.89 | 5.82 |
| 34.43 | 34.56 | 6.66 | 6.76 |
| 31.97 | 32.08 | 7.45 | 7.39 |
| 29.63 | 29.55 | 8.17 | 8.10 |
| 27.48 | 27.29 | 8.87 | 9.01 |
| 22.43 | 22.48 | 10.33 | 10.45 |
| 18.15 | 18.03 | 11.73 | 11.70 |
| 12.86 | 12.96 | 14.62 | 14.68 |
| 6.40 | 6.33 | 15.44 | 15.49 |
| 3.22 | 3.15 | 16.48 | 16.32 |
| 1.75 | 1.82 | 17.04 | 17.11 |
| 0.99 | 0.95 | 17.26 | 17.34 |

Example 13

Figure 18:
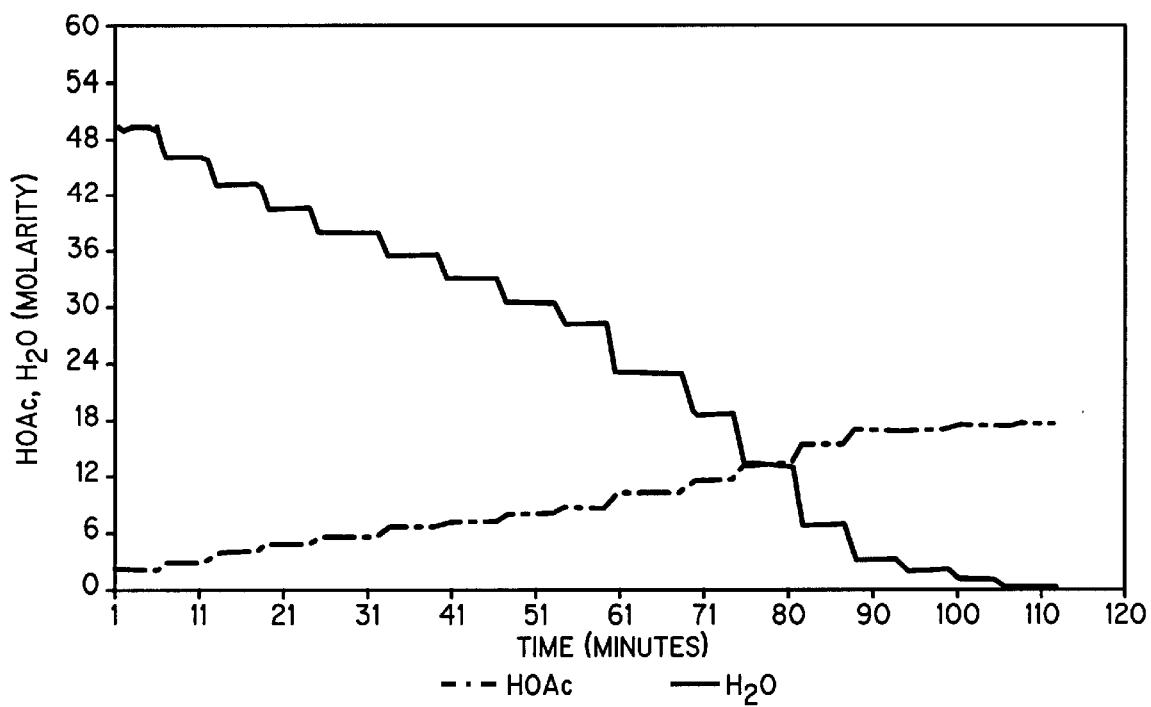
FIG. 18 is a multi-component trend file containing 110 minutes of run time data for two drying column components.

A similar experiment to Example 12 was carried out except that a fiber optic coupled transmission probe as shown in FIG. 4B rather than a transmission cell was used. This one inch diameter, 0.5 mm pathlength probe equipped with sapphire windows was obtained from Axiom Analytical, Irvine, Calif. and was coupled to the FTIR via two 5 meter lengths of low OH silica fiber optic cable obtained from CeramOptec Industries, East Longmeadow, Ma. An Indium Arsenide (InAs) detector was used. The purpose of this experiment was to show that a transmission probe allows similar levels of accuracy and precision as a transmission cell. The trend lines in FIG. 18 and the correlation data in Table 19 indicate that these two methods of sample collection give rise to similar precision and accuracy.

TABLE 19

Addition of HOAc to Drying Column Solution
Correlation of On-Line Extended Mid-Infrared Values
(Transmission Probe) with Independent Off-Line
Analytical Techniques (GC/Karl Fischer)

| H$_2$O (Molarity) | | HOAc (Molarity) | |
| --- | --- | --- | --- |
| Infrared | Karl Fischer | Infrared | GC |
| 49.41 | 49.55 | 1.89 | 1.94 |
| 46.16 | 46.26 | 2.87 | 2.99 |
| 43.20 | 43.22 | 3.97 | 4.06 |
| 40.55 | 40.48 | 4.90 | 4.81 |
| 37.96 | 38.03 | 5.66 | 5.53 |
| 35.50 | 35.42 | 6.38 | 6.50 |
| 33.15 | 33.31 | 7.05 | 7.12 |
| 30.47 | 30.50 | 7.85 | 7.88 |
| 28.32 | 28.22 | 8.51 | 8.44 |
| 22.97 | 22.84 | 10.07 | 10.18 |
| 18.61 | 18.60 | 11.37 | 11.21 |
| 13.35 | 13.27 | 13.31 | 13.34 |
| 6.92 | 6.80 | 15.32 | 15.19 |
| 3.35 | 3.24 | 16.47 | 16.41 |
| 1.98 | 2.05 | 16.84 | 16.98 |
| 1.01 | 0.97 | 17.11 | 17.24 |
| 0.03 | 0.00 | 17.40 | 17.49 |

The above discussion demonstrates that process control of component concentrations for optimization of the manufacture and purification of acetic acid product may be effected by infrared measurements of component concentrations in samples collected continuously from locations in the reaction system downstream of the reactor vessel, with immediate responsive adjustments made in component concentrations, whether directly or indirectly, at an appropriate location in the reaction system. The reaction system includes numerous columns and streams, each of which when fitted with the appropriate monitoring equipment can provide concentration information that informs the system operator where adjustments are needed. The system operator may be an individual or a computerized control system. In other words, the process control can be either manual or automatic. Because the measurements in the process control of the present invention are continuously taken, such as at 30 second to 3 minute intervals, followed by substantially instant adjustment of some process variable in the reaction system, the system operator would advantageously be a computerized control unit that analyzes the incoming data from the infrared analyzer, comparing it to known control limits set for the process variables, and automatically effects the appropriate adjustments to maximize the production of pure acetic acid. Alternatively, the data may be fed to a display unit to be interpreted by an individual who adjusts reaction system components or process variables manually. The adjustments, as stated above, may directly or indirectly alter the concentration of one or more components in one or more locations in the reaction system. Direct adjustment may occur by adding or extracting a component at a location in the reaction system. Indirect adjustment of component concentrations may occur in any number of ways. For example, adjusting the temperature of a solution or the temperature profile in a column affects component concentrations. Decreasing or increasing flow rates of streams from one vessel to another affects component concentrations, not just in those vessels, but may also affect concentrations in other vessels throughout the reaction system. There are many relationships between the different components comprising the solutions in the different locations of the reaction system, as understood by one skilled in the art, and the adjustment of one component concentration at one location in the reaction system can have an effect on more than one component concentration at more than one location in the reaction system. Thus, real time infrared measurement, analysis and adjustment is used in the present invention to control an acetic acid manufacturing process so as to maximize the efficiency and output of the reaction system.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatuses and methods and illustrative examples shown and described. Accordingly, departures may be made from such details without departing from the scope or spirit of applicant's general inventive concept.

What is claimed is:

1. A method of effecting process control of component concentrations in a reaction system for the production of acetic acid from the carbonylation of methanol, comprising:

collecting a reaction system sample from downstream of a reactor vessel in the reaction system, the sample comprising at least one component selected from the group consisting of water, acetic acid, methyl acetate, methyl iodide, acetaldehyde, hydrocarbons, propionic acid, hydrogen iodide and mixtures thereof;

measuring the concentration of at least one of said components in an infrared analyzer; and adjusting a component concentration in the reaction system in at least one of the reactor vessel, a downstream column or a downstream transfer line in the reaction system in response to the measured concentration.

2. The method of claim 1 wherein the adjusting is accomplished directly by adding or removing a component from at least one of the reactor vessel, a downstream column or a downstream transfer line in the reaction system.

3. The method of claim 1 wherein the adjusting is accomplished indirectly by adjusting in at least one of the reactor vessel, a downstream column or a downstream transfer line in the reaction system at least one of a temperature of a reaction system solution, a temperature profile in a column, a flow rate of a reaction system solution or a vent gas rate.

4. The method of claim 1 comprising collecting the sample from a heavy phase of a light ends recovery decanter column and measuring in the infrared analyzer the density of the heavy phase and the concentration of hydrocarbons in the sample and adjusting a flow rate of the heavy phase to at least one of a hydrocarbons removal column and an alkanes removal column in response to the measurements of the density and the concentration of hydrocarbons.

5. The method of claim 1 comprising collecting the sample from a heavy phase of a light ends recovery decanter column and measuring in the infrared analyzer at least one of the concentration of methyl iodide and methyl acetate in the heavy phase and adjusting at least one of a flow rate to the reactor vessel of the heavy phase and a light phase in the light ends recovery decanter in response to the measured methyl iodide or methyl acetate concentration.

6. The method of claim 1 comprising collecting the sample from at least one of a heavy phase and a light phase of a light ends recovery decanter column and measuring in the infrared analyzer the concentration of acetaldehyde in the sample and adjusting at least one of a water feed rate into the reactor vessel, a vent gas rate out of the reactor vessel, and a flow rate of the light phase to an acetaldehyde removal system in response to the measured acetaldehyde concentration.

7. The method of claim 1 comprising collecting the sample from a light phase of a light ends recovery decanter column and measuring in the infrared analyzer at least one of the concentration of water and the concentration of acetic acid in the sample and adjusting at least one of a flow rate of the light phase to a light ends column, a flow rate of the light phase to the reactor vessel and the temperature of a solution in the light ends column in response to the measured concentration of water or acetic acid.

8. The method of claim 1 comprising collecting the sample from a bottoms of a light ends column and measuring in the infrared analyzer at least one of the concentration of water and the concentration of hydrogen iodide in the sample and adjusting a flow rate of a stream comprising water into the light ends column in response to the measured concentration of water or hydrogen iodide.

9. The method of claim 1 comprising collecting the sample from a feed stream to a drying column and measuring in the infrared analyzer the concentration of water in the sample and adjusting at least one of a feed rate of a light phase from a light ends recovery decanter column to a light ends column and a feed rate of water to the reactor vessel in response to the measured concentration of water.

10. The method of claim 1 comprising collecting the sample from a heavy ends column and measuring in the infrared analyzer the concentration of propionic acid in the sample and adjusting at least one of a water feed rate into the reactor vessel and a vent gas rate out of the reactor vessel in response to the measured concentration of propionic acid.

11. The method of claim 1 comprising collecting the sample from a heavy ends column and measuring in the infrared analyzer the concentration of water in the sample and adjusting the temperature profile in a drying column in response to the measured concentration of water.

12. The method of claim 1 comprising collecting the sample from at least one of a feed stream, a product output stream, a bottoms waste stream and an overhead output stream of a heavy ends column and measuring in the infrared analyzer the concentration of propionic acid in the sample and adjusting at least one of the temperature profile in the heavy ends column, a flow rate from a heavy ends column overhead drum to the heavy ends column, a flow rate from the overhead drum to a drying column, a flow rate of the bottoms waste stream and a flow rate of the product output stream in response to the measured concentration of propionic acid.

13. The method of claim 1 wherein the infrared analyzer is a Fourier Transform infrared spectrometer.

14. The method of claim 1 wherein the infrared analyzer operates in one of a mid-infrared region and a near-infrared region.

15. The method of claim 1 further comprising transmitting the measured concentrations to a control unit for real time analysis.

16. The method of claim 15 wherein the adjusting is substantially instantly after the measuring and analysis.

17. The method of claim 1 wherein the measuring and adjusting is performed about every 30 seconds to 3 minutes.

18. A method of effecting process control of component concentrations in a reaction system for the production of acetic acid from the carbonylation of methanol, comprising:
    collecting a reaction system sample from a heavy phase of a light ends recovery decanter vessel downstream of a reactor vessel in the reaction system, the sample comprising the components of water, acetic acid, methyl acetate, methyl iodide, acetaldehyde and hydrocarbons;
    measuring at least one of the density of the sample and the concentration of at least one of said components in an infrared analyzer; and
    adjusting at least one of the following in response to the measured concentration or density:
        (a) the flow rate of a recycle stream to the reaction section;
        (b) the flow rate of the heavy phase to an acetaldehyde removal system;
        (c) the flow rate of the heavy phase to a hydrocarbons removal column;
        (d) the feed rate of water to the reactor vessel;
        (e) the vent gas rate out of the reactor vessel.

19. The method of claim 18 wherein the recycle stream in (a) is from a light phase of the decanter vessel to the reactor vessel.

20. The method of claim 18 wherein the recycle stream in (a) is from the heavy phase of the decanter vessel to the reactor vessel.

21. The method of claim 18 wherein the recycle stream in (a) is from a drying column overhead to the reactor vessel.

22. The method of claim 18 wherein the recycle stream in (a) is from a light ends column to a flash tank.

23. The method of claim 18 wherein the recycle stream in (a) is from a hydrocarbons removal column to a flash tank.

24. The method of claim 18 wherein the infrared analyzer is a Fourier Transform infrared spectrometer.

25. The method of claim 18 wherein the infrared analyzer operates in one of a mid-infrared region and a near-infrared region.

26. The method of claim 18 further comprising transmitting the measured concentrations to a control unit for real time analysis.

27. The method of claim 26 wherein the adjusting is substantially instantly after the measuring and analysis.

28. The method of claim 18 wherein the measuring and adjusting is performed about every 30 seconds to 3 minutes.

29. The method of claim 18 comprising adjusting only (a) in response to the measured concentration or density.

30. The method of claim 18 comprising adjusting only (b) in response to the measured concentration or density.

31. The method of claim 18 comprising adjusting only (c) in response to the measured concentration or density.

32. The method of claim 18 comprising adjusting only (d) in response to the measured concentration or density.

33. The method of claim 18 comprising adjusting only (e) in response to the measured concentration or density.

34. A method of effecting process control of component concentrations in a reaction system for the production of acetic acid from the carbonylation of methanol, comprising:
    collecting a reaction system sample from a light phase of a light ends recovery decanter vessel downstream of a reactor vessel in the reaction system, the sample comprising the components of water, acetic acid, methyl acetate, methyl iodide and acetaldehyde;
    measuring at least one of the density of the sample and the concentration of at least one of said components in an infrared analyzer; and
    adjusting at least one of the following in response to the measured concentration or density:
        (a) the flow rate of the light phase to the reactor vessel;
        (b) the flow rate of the light phase to a light ends column;
        (c) the temperature of a solution in a light ends column;
        (d) the feed rate of water to the reactor vessel;
        (e) the vent gas rate out of the reactor vessel;
        (f) the flow rate of the light phase to an acetaldehyde removal system.

35. The method of claim 34 wherein the infrared analyzer is a Fourier Transform infrared spectrometer.

36. The method of claim 34 wherein the infrared analyzer operates in one of a mid-infrared region and a near-infrared region.

37. The method of claim 34 further comprising transmitting the measured concentrations to a control unit for real time analysis.

38. The method of claim 37 wherein the adjusting is substantially instantly after the measuring and analysis.

39. The method of claim 34 wherein the measuring and adjusting is performed about every 30 seconds to 3 minutes.

40. The method of claim 34 comprising adjusting only (a) in response to the measured concentration or density.

41. The method of claim 34 comprising adjusting only (b) in response to the measured concentration or density.

42. The method of claim 34 comprising adjusting only (c) in response to the measured concentration or density.

43. The method of claim 34 comprising adjusting only (d) in response to the measured concentration or density.

44. The method of claim 34 comprising adjusting only (e) in response to the measured concentration or density.

45. The method of claim 34 comprising adjusting only (f) in response to the measured concentration or density.

46. A method of effecting process control of component concentrations in a reaction system for the production of acetic acid from the carbonylation of methanol, comprising:
collecting a sample from a bottom portion of a light ends column downstream of a reactor vessel in the reaction system, the sample comprising the components of water, acetic acid and hydrogen iodide;
measuring the concentration of at least one of said components in an infrared analyzer; and
adjusting the temperature of a solution in the light ends column in response to the measured concentration.

47. The method of claim 46 wherein the infrared analyzer is a Fourier Transform infrared spectrometer.

48. The method of claim 46 wherein the infrared analyzer operates in one of a mid-infrared region and a near-infrared region.

49. The method of claim 46 further comprising transmitting the measured concentrations to a control unit for real time analysis.

50. The method of claim 49 wherein the adjusting is substantially instantly after the measuring and analysis.

51. The method of claim 46, wherein the measuring and adjusting is performed about every 30 seconds to 3 minutes.

52. A method of effecting process control of component concentrations in a reaction system for the production of acetic acid from the carbonylation of methanol, comprising:
collecting a reaction system sample from a feed stream to a drying column downstream of a reactor vessel in the reaction system, the sample comprising the components of water and acetic acid;
measuring the concentration of at least one of said components in an infrared analyzer; and
adjusting at least one of the following in response to the measured concentration:
(a) the flow rate of a light phase from a light ends recovery decanter column to a light ends column; and
(b) the feed rate of water to the reactor vessel.

53. The method of claim 52 wherein the infrared analyzer is a Fourier Transform infrared spectrometer.

54. The method of claim 52 wherein the infrared analyzer operates in one of a mid-infrared region and a near-infrared region.

55. The method of claim 52 further comprising transmitting the measured concentrations to a control unit for real time analysis.

56. The method of claim 55 wherein the adjusting is substantially instantly after the measuring and analysis.

57. The method of claim 52 wherein the measuring and adjusting is performed about every 30 seconds to 3 minutes.

58. The method of claim 52 comprising adjusting only (a) in response to the measured concentration or density.

59. The method of claim 52 comprising adjusting only (b) in response to the measured concentration or density.

60. A method of effecting process control of component concentrations in a reaction system for the production of acetic acid from the carbonylation of methanol, comprising:
collecting a reaction system sample from at least one of a heavy ends column downstream of a reactor vessel in the reaction system, a feed stream to the heavy ends column, a product output stream out of the heavy ends column, a bottoms waste stream out of the heavy ends column and an overhead output stream out of the heavy ends column, the sample comprising the components of water, acetic acid and propionic acid;
measuring the concentration of at least one of said components in an infrared analyzer; and
adjusting at least one of the following in response to the measured concentration:
(a) a flow rate from the overhead output stream back to the heavy ends column;
(b) a flow rate from the overhead output stream to a drying column;
(c) a flow rate of the bottoms waste stream;
(d) a flow rate of the product output stream;
(e) the temperature profile in a drying column;
(f) the temperature profile in the heavy ends column;
(g) a feed rate of water to the reactor vessel;
(h) a vent gas rate out of the reactor vessel.

61. The method of claim 60 wherein the infrared analyzer is a Fourier Transform infrared spectrometer.

62. The method of claim 60 wherein the infrared analyzer operates in one of a mid-infrared region and a near-infrared region.

63. The method of claim 60 further comprising transmitting the measured concentrations to a control unit for real time analysis.

64. The method of claim 63 wherein the adjusting is substantially instantly after the measuring and analysis.

65. The method of claim 60 wherein the measuring and adjusting is performed about every 30 seconds to 3 minutes.

66. The method of claim 60 comprising adjusting only (a) in response to the measured concentration or density.

67. The method of claim 60 comprising adjusting only (b) in response to the measured concentration or density.

68. The method of claim 60 comprising adjusting only (c) in response to the measured concentration or density.

69. The method of claim 60 comprising adjusting only (d) in response to the measured concentration or density.

70. The method of claim 60 comprising adjusting only (e) in response to the measured concentration or density.

71. The method of claim 60 comprising adjusting only (f) in response to the measured concentration or density.

72. The method of claim 60 comprising adjusting only (g) in response to the measured concentration or density.

73. The method of claim 60 comprising adjusting only (h) in response to the measured concentration or density.

* * * * *

UNITED STATES PATENT AND TRADEMARK OFFICE
CERTIFICATE OF CORRECTION

PATENT NO.   : 6,552,221 B1
DATED        : April 22, 2003
INVENTOR(S)  : Hallinan et al.

It is certified that error appears in the above-identified patent and that said Letters Patent is hereby corrected as shown below:

Title page,
Item [73], "Millenium" should be -- Millennium --.

Column 1,
Lines 8 and 9, "allowed and entitled which" should be -- entitled MANUFACTURING AND PROCESS CONTROL METHODS, which --.

Column 2,
Line 65, "a mother" should be -- another --.

Column 3,
Line 19, "is multi-component" should be -- is a multi-component --.

Column 5,
Line 44, "areas," should be -- areas: --.

Column 6,
Line 29, "while is" should be -- while this --.

Column 18,
Line 25, "on-line line infrared" should be -- on-line infrared --.

Column 19,
Line 44, "to Acetaldehyde" should be -- of Acetaldehyde --.

Column 20,
Line 20, "to Acetaldehyde" should be -- of Acetaldehyde --.

UNITED STATES PATENT AND TRADEMARK OFFICE
CERTIFICATE OF CORRECTION

PATENT NO. : 6,552,221 B1
DATED : April 22, 2003
INVENTOR(S) : Hallinan et al.

It is certified that error appears in the above-identified patent and that said Letters Patent is hereby corrected as shown below:

Column 26,
Line 23, "of+/-0.1" should be -- of +/-0.1 --.

Signed and Sealed this

Eighteenth Day of November, 2003

JAMES E. ROGAN
*Director of the United States Patent and Trademark Office*